(12) United States Patent
Fox et al.

(10) Patent No.: US 12,733,836 B2
(45) Date of Patent: Sep. 15, 2026

(54) EXTRACORPOREAL ASPIRANT DETECTION SYSTEMS AND METHODS

(71) Applicant: Fox Medical Systems, LLC, Houston, TX (US)

(72) Inventors: Steven Fox, El Paso, TX (US); Gino Morello, Leonia, NJ (US); David Leak, Minnestrista, MN (US); Robert Orlean, Houston, TX (US); Bryan Lynch, Houston, TX (US)

(73) Assignee: Fox Medical Systems, LLC, Houston, TX (US)

( * ) Notice: Subject to any disclaimer, the term of this patent is extended or adjusted under 35 U.S.C. 154(b) by 99 days.

(21) Appl. No.: 18/772,232

(22) Filed: Jul. 14, 2024

(65) Prior Publication Data

US 2025/0152038 A1 May 15, 2025

Related U.S. Application Data

(60) Provisional application No. 63/670,594, filed on Jul. 12, 2024, provisional application No. 63/607,050,
(Continued)

(51) Int. Cl.
*A61B 5/00* (2006.01)
*A61B 5/08* (2006.01)
(Continued)

(52) U.S. Cl.
CPC .......... *A61B 5/0803* (2013.01); *A61B 5/0077* (2013.01); *A61B 5/277* (2021.01);
(Continued)

(58) Field of Classification Search
CPC ..... A61B 5/0803; A61B 5/0077; A61B 5/277; A61B 5/6802; A61B 5/742; A61B 5/7455;
(Continued)

(56) References Cited

U.S. PATENT DOCUMENTS

| | | | |
|---|---|---|---|
| 6,840,242 | B1 | 1/2005 | McCoy |
| 11,471,876 | B2 | 10/2022 | Ott et al. |

(Continued)

FOREIGN PATENT DOCUMENTS

| | | | | |
|---|---|---|---|---|
| JP | 5952536 | | 7/2016 | |
| KR | 20220122067 A | * | 9/2022 | ............ A61B 90/39 |

(Continued)

OTHER PUBLICATIONS

Cheng,"Active capacitive sensing: Exploring a new wearable sensing modality for activity recognition." International conference on pervasive computing. Berlin, Heidelberg: Springer Berlin Heidelberg, 2010. (Year: 2010).*

(Continued)

*Primary Examiner* — Michael J Carey
*Assistant Examiner* — Zainab Mohammed Aldarraji
(74) *Attorney, Agent, or Firm* — McAughan Deaver PLLC

(57) ABSTRACT

An extracorporeal aspirant prediction and detection system and methods for same are disclosed in which an external sensor assembly, such as a collar-like structure, is placed or worn on the neck and comprises a plurality of integral sensors and/or sensor types for detection of a foreign substance, such as aspirant. Electronic signal conditioning and processing systems, a power source, and communication elements are provided for alerting the user or clinician of any aspiration events.

30 Claims, 20 Drawing Sheets

Related U.S. Application Data filed on Dec. 6, 2023, provisional application No. 63/513,641, filed on Jul. 14, 2023.

(51) Int. Cl.
*A61B 5/277* (2021.01)
*A61B 8/00* (2006.01)
*A61B 8/08* (2006.01)

(52) U.S. Cl.
CPC ............ *A61B 5/6802* (2013.01); *A61B 5/742* (2013.01); *A61B 5/7455* (2013.01); *A61B 8/08* (2013.01); *A61B 8/4209* (2013.01)

(58) Field of Classification Search
CPC ....... A61B 8/08; A61B 8/4209; A61B 5/0086; A61B 5/08; A61B 5/285; A61B 5/4205
See application file for complete search history.

(56) References Cited

U.S. PATENT DOCUMENTS

2012/0150073 A1 6/2012 Dunn et al.
2016/0026767 A1* 1/2016 Sarrafzadeh ............ A61B 5/48 600/593
2018/0000402 A1 1/2018 Omari
2020/0170650 A1 6/2020 Shaker et al.
2020/0268307 A1* 8/2020 Ohta ........................ G01B 7/16
2021/0068740 A1 3/2021 Rieger et al.
2021/0128069 A1 5/2021 Telfort
2021/0178223 A1 6/2021 Gaboriault
2022/0054361 A1 2/2022 Lin
2022/0111204 A1 4/2022 Ueno et al.
2022/0125372 A1 4/2022 Jedwab et al.
2022/0133596 A1 5/2022 Tabor
2022/0184379 A1 6/2022 Lindenthaler et al.
2022/0273228 A1 9/2022 Nicolini

FOREIGN PATENT DOCUMENTS

WO WO-2018207935 A1 * 11/2018 ........... A61B 8/4477
WO 2022085188 A1 4/2022

OTHER PUBLICATIONS

Google, Translation of JP5952536, Feb. 5, 2026, Internet.
Google, Translation of WO2022085188, Feb. 5, 2026, Internet.
PCT, International Search Report and Written Opinion for PCT/US2024/037970, Jul. 14, 2024.

* cited by examiner

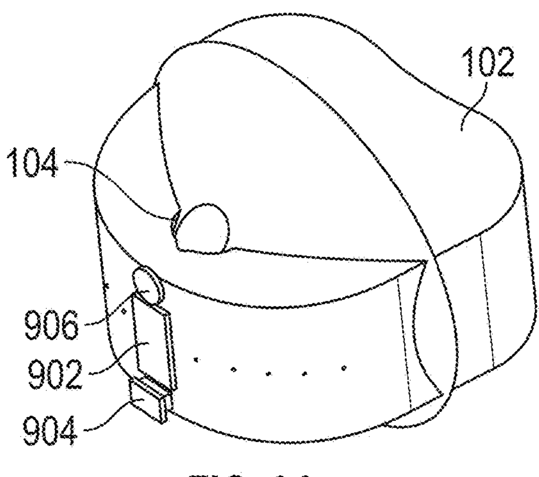
FIG. 9A
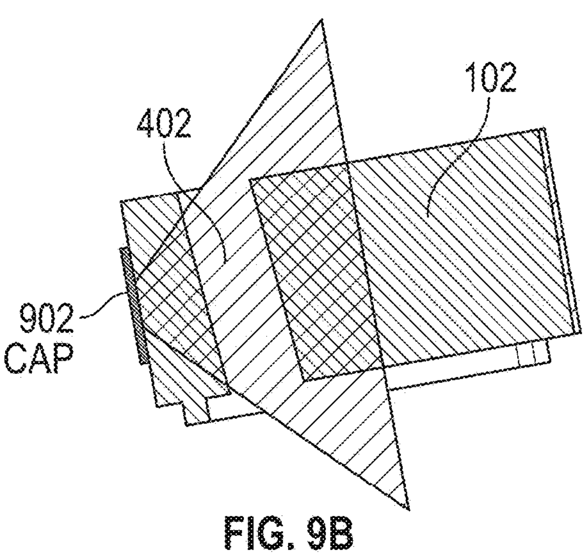
FIG. 9B
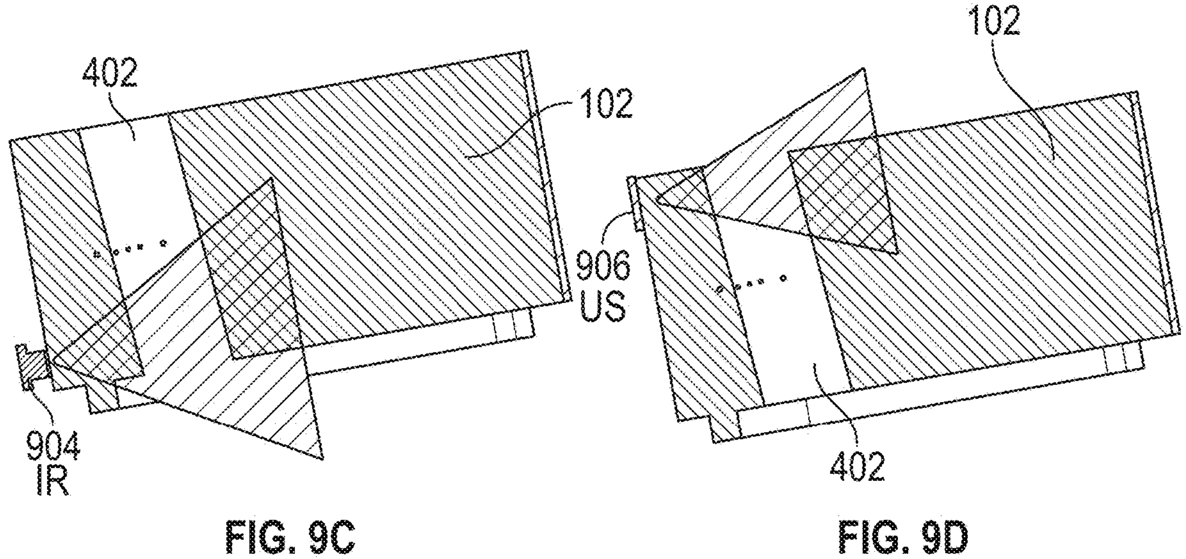
FIG. 9C
FIG. 9D

EXTRACORPOREAL ASPIRANT DETECTION SYSTEMS AND METHODS

CROSS REFERENCE TO RELATED APPLICATIONS

This application claims benefit of and priority to the following commonly owned US applications: U.S. provisional application No. 63/513,641 filed on Jul. 14, 2023; U.S. provisional application No. 63/607,050 filed on Dec. 6, 2023, and U.S. provisional application No. 63/670,594 filed on Jul. 12, 2024, the entire contents of each of which are incorporated herein by reference for all purposes.

STATEMENT REGARDING FEDERALLY SPONSORED RESEARCH OR DEVELOPMENT

Not applicable.

REFERENCE TO APPENDIX

Not applicable.

BACKGROUND OF THE INVENTION

Field of the Invention The inventions disclosed herein relate to the detection and/or prediction of aspiration events in patients having some level or form of dysphagia.

Description of the Related Art Dysphagia is the medical term for a swallowing deficiency or insufficiency. Successful swallowing involves many interrelated systems, including muscles and nerves, to move food and/or liquid (i.e., bolus) from mouth to stomach. Dysphagia occurs when these interrelated systems do not function properly and may occur in the mouth (i.e., oral dysphagia), in the throat (i.e., oropharyngeal dysphagia) or in the esophagus (i.e., esophageal dysphagia). When swallowing is not successful, that is, when bolus is not successfully moved from the mouth to the stomach, it can be a sign of serious condition. Dysphagia is a common symptom following a stroke. Undetected or untreated dysphagia risks food or liquid getting into the airway or trachea, which is referred to as aspiration. If not timely expelled from the trachea/lungs, such aspirants may lead to pneumonia, other diseases, or death.

Patients with dysphagia often live in fear of aspirating food or fluid into their lungs. When eating, dysphagia patients are in a heightened state of cautiousness and tend to play with their food and take small bites to avoid aspiration. They are unable to enjoy their meal for fear of aspiration. It is common for patients to prophylactically cough as they eat as a preventative measure. Every meal may become an ordeal for the patient, family, and friends.

While attempts have been made to detect and treat dysphagia, and/or train swallowing techniques, there is room for improvement. For example, US Published Patent Application No. 2012/0089045 is entitled Measurement system for evaluating the swallowing process and/or for detecting aspiration and discloses "the use of measurement system for evaluating a swallowing process, preferably a closure of the airway during the swallowing process and/or an aspiration. The measurement system can be used for supporting therapy in case of swallowing disorders and/or for diagnosing changes in swallowing sequence."

US Published Patent Application No. 2005/0283096 is entitled Apparatus and method for detecting swallowing activity and discloses "[a]n apparatus and method for detecting swallowing activity is provided. In an embodiment, a method includes receiving an electronic signal from an accelerometer that represents swallowing activity, extracting at least two features from the signal, classifying the signal as a type of swallowing activity based on the extracted features, and generating an output of the classification. Exemplary activities include swallows, aspirations, movement and vocal artifacts. By indicating whether an activity is a swallow or an aspiration, the manner in which a patient afflicted with an increased likelihood for aspirations is fed can be adjusted to increase the likelihood of achieving a swallow instead of an aspiration during feeding. In turn this could reduce hospitalizations for aspiration pneumonia in patients with acute or chronic injury."

US Published Patent Application No. 2012/0150073 is entitled Method and apparatus for diagnosing a medical condition based upon audial data from a patient and discloses "[a] system is provided that is operable to obtain acoustic data from a patient and analyze the data to diagnose whether a patient has a medical condition. In one embodiment, an acoustic detector obtains acoustic data from a patient swallowing and communicates the information with an acoustic processor. The processor analyzes the data by comparing the acoustic data to evaluate the presence of one or more acoustic features to determine the presence or absence of aspiration during swallowing."

PCT Published Application WO 2018/207935 is entitled Swallowing-related information acquisition apparatus, information analysis method, and program and discloses "[a]n apparatus for acquiring swallowing-related information includes an ultrasound transmitting device that transmits ultrasound waves to a larynx and/or trachea area of a subject, an ultrasound receiving device that converts the ultrasound waves transmitted through the larynx and/or trachea area of the subject to received signals, an attachment device that holds the ultrasound transmitting device and the receiving device on the neck of the subject such that the ultrasound waves pass through the larynx and/or trachea area of the subject, a processing device including circuitry that coverts the received signals into swallowing-related information, detects at least one swallowing-related event and biological information based on the swallowing-related information, analyzes at least one swallowing-related event and the biological information to generate swallowing related information analysis, and generates information for safety and dysphagia rehabilitation based on the swallowing-related information analysis including an alert system activation that activates alert system to inform aspiration of the subject. The swallowing-related event includes at least one selected from the group consisting of dysphasia, abnormal swallowing, and cough, and the biological information includes at least one selected from the group consisting of body temperature, pulse rate, respiration rate, blood pressure, mastication-related information, vocalization, and movement of the neck."

Thus, we see the need for extracorporeal systems and methods that can reliably predict aspiration events and/or reliably detect aspiration events to minimize or avoid aspiration events.

It is to be understood that the discussion above is provided for illustrative purposes only and is not intended to and does not limit the scope or subject matter of the appended disclosure or ultimately issued claims or those of any related patent application or patent. Thus, none of the disclosure, appended claims, ultimately issued claims or claims of any related application or patent are to be limited by the above discussion or construed to address, include, or exclude each or any of the above-cited features or disadvantages merely because such were mentioned herein.

BRIEF SUMMARY OF THE INVENTION

A brief summary of the inventions, which indicates their nature and substance may be understood from the scope of the subject matter encompassed by the appended claims and their equivalents, which are incorporated herein by reference for all purposes of this summary Also, a brief summary of the inventions, which indicates their nature and substance may be understood from the scope of the subject matter encompassed by any claims that may be issued from this application and their equivalents, which claims also are incorporated herein by reference for all purposes of this summary This Brief Summary Of The Invention is not intended to and does not summarize all the inventions that are enabled by this specification.

Without prejudice or waiver to the inventions disclosed and enabled by this specification, our inventions may comprise but are not limited to a system for detecting aspiration, which may comprise a sensor assembly that has a body with an outer surface and an inner surface. The inner surface may be shaped to conform to an anterior portion of a human neck. A first sensor of a first sensor type may be disposed in the body such that an operative surface of the first sensor may be exposed on the inner surface of the body. A second sensor of a second sensor type may be disposed in the body such that an operative surface of the second sensor may be exposed on the inner surface of the body. When the sensor assembly may be placed in contact with the anterior portion of the human neck, the operative surfaces of the first and second sensors operatively contact epidermis be of the human neck. The first and second sensors are located and orientated in the sensor assembly so that the first and second sensors can detect the presence and/or the absence of aspirant in a trachea associated with the neck. A data processing assembly may be organized to receive data from the first and second sensors and may be operative to determine the presence or absence of aspirant in the trachea and to visually, audibly, and/or physically indicate the presence of aspirant in the trachea.

Additionally, optionally, or alternately, the first sensor may comprise a capacitive sensor and the second sensor may comprise an infrared sensor. The capacitive sensor may be operated at a frequency of between 3 kHz and 3 GHZ. The first sensor may comprise a plurality of individual capacitive sensors, each may be operated at a frequency of between 3 kHz and 3 GHz. The plurality of individual capacitive sensors may be located in the sensor assembly and may be oriented with respect to the trachea to detect the presence of aspirant, a characteristic of the aspirant, and/or a direction of travel of the aspirant. The infrared sensor may be operated to emit radiation at wavelengths of between 835 nm to 940 nm The second sensor may comprise a plurality of individual infrared sensors, each individual sensor may be operated to emit radiation at wavelengths of between 835 nm to 940 nm The plurality of individual infrared sensors may be in the sensor assembly and oriented with respect to the trachea to detect the presence of aspirant, a characteristic of the aspirant, a direction of travel of the aspirant, and/or an image of the aspirant. The first sensor may comprise a plurality of individual capacitive sensors, each individual capacitive sensor may be operated at a frequency of between 3 kHz and 3 GHZ, the second sensor may comprise a plurality of individual infrared sensors, each individual infrared sensor may be operated to emit radiation at wavelengths of between 835 nm to 940 nm, and the first and second sensors may be located in the sensor assembly and oriented with respect to the trachea to detect the presence of aspirant, a characteristic of the aspirant, a direction of travel of the aspirant, and/or an image of the aspirant.

Additionally, optionally or alternately, the first sensor may comprise a capacitive sensor and the second sensor may comprise an ultrasonic sensor. The first sensor may comprise a plurality of individual capacitive sensors, each may be operated at a frequency of between 3 kHz and 3 GHz. The plurality of individual capacitive sensors may be in the sensor assembly and oriented with respect to the trachea to detect the presence of aspirant, a characteristic of the aspirant and/or a direction of travel of the aspirant. The second sensor may comprise a plurality of individual ultrasonic sensors, each individual sensor may be operated to emit sound at frequencies of between 1 MHz and 5 MHz. The plurality of individual ultrasonic sensors may be in the sensor assembly and oriented with respect to the trachea to detect the presence of aspirant, a characteristic of the aspirant, a direction of travel of the aspirant, and/or an image of the aspirant. The first sensor may comprise a plurality of individual capacitive sensors, each individual capacitive sensor may be operated at a frequency of between 3 kHz and 3 GHZ, the second sensor may comprise a plurality of individual ultrasonic sensors, each individual ultrasonic sensor may be operated to emit sound at a frequency of between 1 MHz and 5 MHz, and wherein the first and second sensors are located in the sensor assembly and oriented with respect to the trachea to detect the presence of aspirant, a characteristic of the aspirant, a direction of travel of the aspirant, and/or an image of the aspirant. The presence of aspirant may be indicated to the wearer of the sensor assembly. The data processing assembly may be housed within the sensor assembly. The data processing assembly may be separate from and remote to the sensor assembly. The data processing assembly may be wired to the sensor assembly for data transmission and power supply. The presence of aspirant may be indicated to a clinician using the system on a patient.

Without prejudice or waiver to the inventions disclosed and enabled by this specification, our inventions may comprise but are not limited to a method of detecting the presence of aspirant, which may comprise providing a body having an inner surface shaped to conform to an anterior portion of a human neck. Locating a first sensor in the body so that an operative surface of the first sensor contacts a first portion of the neck when the inner surface may be placed on the neck. Locating a second sensor in the body so that an operative surface of the second sensor contacts a second portion of the neck when the operative portion of the first sensor contacts the first portion of the neck. Orienting the first and second sensors in the body so that a field of detection of each sensor encompasses at least a portion of a trachea within the neck. Energizing the first and second sensors to generate the first sensor detection field and the second sensor detection field. Processing data from the first and second sensors to detect the presence or absence of aspirant. Automatically indicating the presence of aspirant by one or more of: a visual indication, an audible indication, or a physical indication.

Additionally, optionally or alternately, first sensor may comprise capacitive sensor and the second sensor may comprise an infrared sensor. The first sensor may comprise a capacitive sensor and the second sensor may comprise an ultrasonic sensor. The first sensor may comprise a capacitive sensor and the second sensor may comprise an infrared sensor and locating an ultrasonic sensor in the body so that an operative surface of the ultrasonic sensor contacts a third portion of the neck when the operative portion of the first and second sensors contact the neck. The capacitive sensor, the infrared sensor and the ultrasonic sensor may be oriented such that their respective detection fields traverse substantially the same region of trachea. Processing data from the first and second sensors may be done remotely from the body. Processing data from the first and second sensors may be done within the body. Automatically indicating may comprise vibrating at least a portion of the body. Automatically indicating may comprise visually indicating on a device separate from and remote to the body. The device may be one or more of: a smart phone, a smart tablet, or a computer.

BRIEF DESCRIPTION OF THE SEVERAL VIEWS OF THE DRAWINGS

The following figures are part of the disclosure of inventions and are included to further disclose and enable certain aspects of the inventions. The inventions may be better understood by reference to one or more of these figures in combination with the detailed description of certain embodiments presented herein.

FIGS. 9A-9D illustrate alternative sensor placements and detection overlaps about the neck region to detect and/or predict aspiration.

Figure 1A:
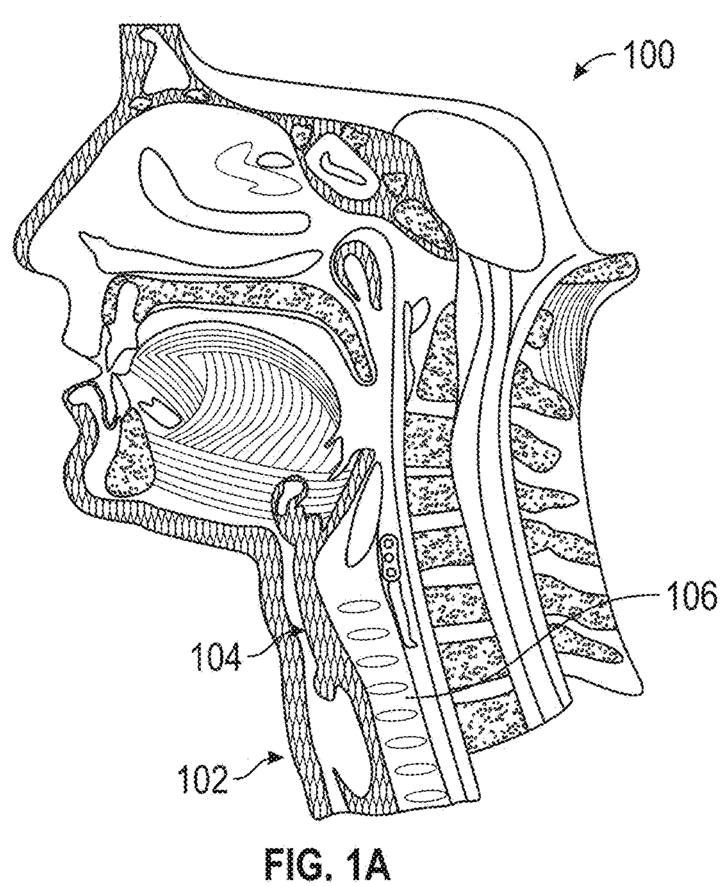
FIGS. 1A and 1B illustrate typical anatomy of a human head and neck region including the trachea, lumen of trachea and esophagus.
Figure 1B:
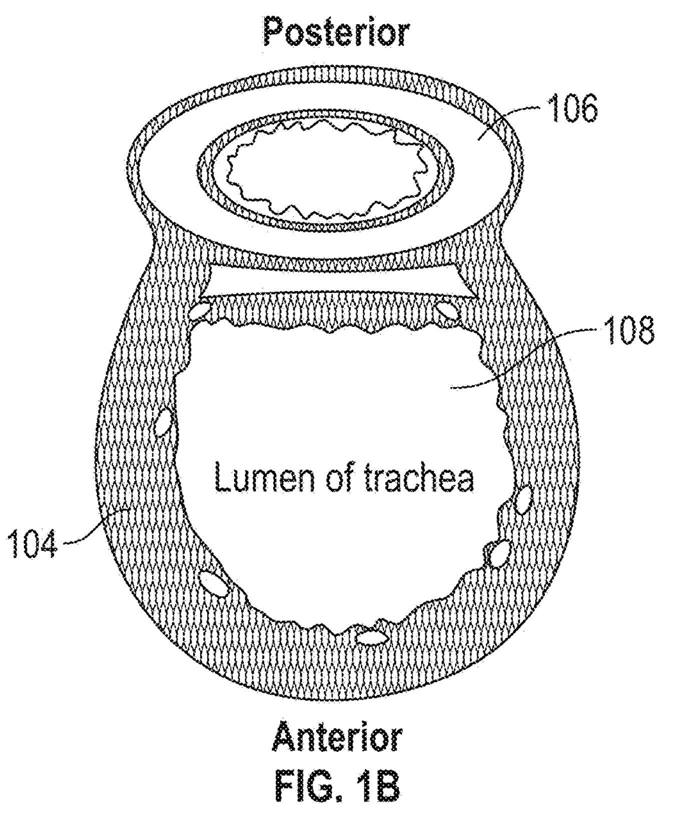
Figure 1C:
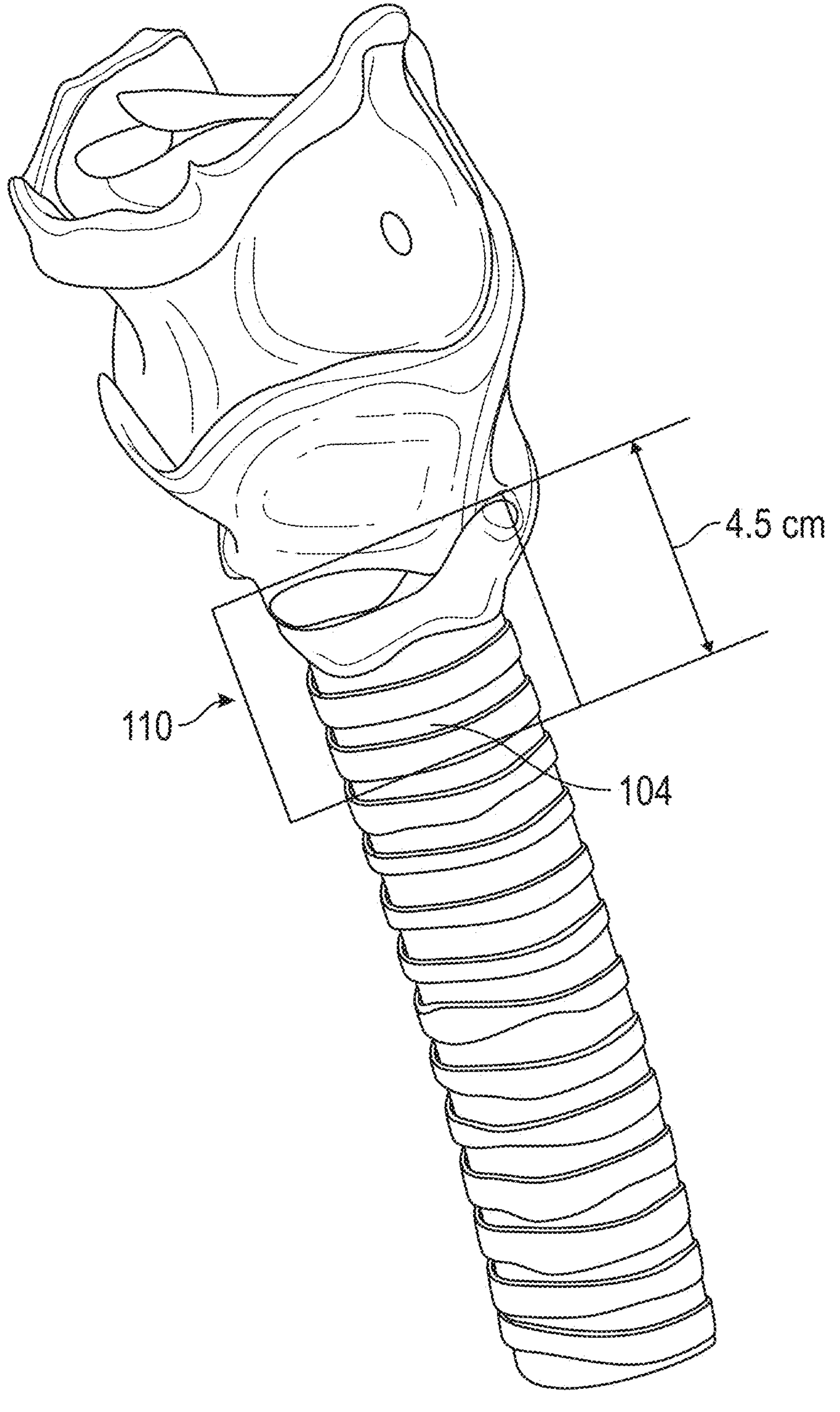
FIGS. 1C and 1D illustrate a preferred sensor placement relative to a human trachea for detecting aspiration events.
Figure 1D:
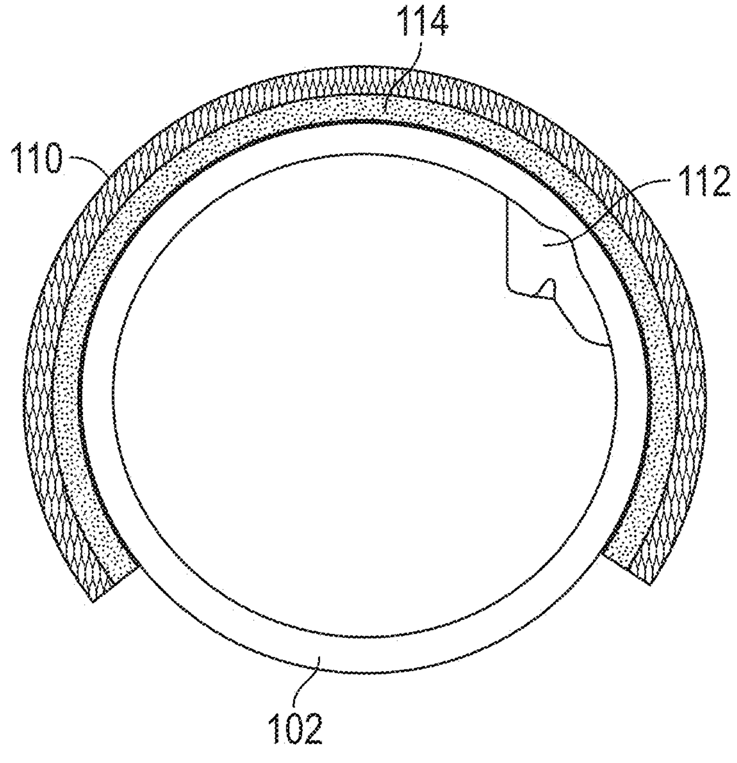

While the inventions disclosed herein are susceptible to various modifications and alternative forms, only a few specific embodiments have been shown by way of example in the drawings and are described in more detail below. The figures and detailed descriptions of these embodiments are not intended to limit the breadth or scope of the inventive concepts disclosed and enabled or the appended claims in any manner Rather, the figures and detailed written descriptions are provided to illustrate the inventive concepts to a person of ordinary skill in the art and to enable such person to make and use the inventive concepts illustrated and taught by the specific embodiments.

DETAILED DISCLOSURE

A person of skill in this art that has benefit of this disclosure (which includes the attachments hereto) will understand that the inventions are disclosed and taught herein by reference to specific embodiments, and that these specific embodiments are susceptible to numerous and various modifications and alternative forms without departing from the inventions we possess. For example, and not limitation, a person of skill in this art that has benefit of this disclosure will understand that Figures and/or embodiments that use one or more common structures or elements, such as a structure or an element identified by a common reference number, are linked together for all purposes of supporting and enabling our inventions, and that such individual Figures or embodiments are not disparate disclosures. A person of skill in this art that has benefit of this disclosure immediately will recognize and understand the various other embodiments of our inventions having one or more of the structures or elements illustrated and/or described in the various linked embodiments. In other words, not all possible embodiments of our inventions are described or illustrated in this application, and one or more of the claims to our inventions may not be directed to a specific, disclosed example. Nonetheless, a person of skill in this art that has benefit of this disclosure will understand that the claims are fully supported by the entirety of this disclosure.

Those persons skilled in this art will appreciate that not all features of a commercial embodiment of the inventions are described or shown for the sake of clarity and understanding. Persons of skill in this art will also appreciate that the development of an actual commercial embodiment incorporating aspects of the present inventions will require numerous implementation-specific decisions to achieve the developer's ultimate goal for the commercial embodiment. Such implementation-specific decisions may include, and likely are not limited to, compliance with system-related, business-related, government-related, and other constraints, which may vary by specific implementation, location and from time to time. While a developer's efforts might be complex and time-consuming in an absolute sense, such efforts would be, nevertheless, a routine undertaking for those of skill in this art having benefit of this disclosure.

Further, the use of a singular term, such as, but not limited to, "a," is not intended as limiting of the number of items. Also, the use of relational terms, such as, but not limited to, "top," "bottom," "left," "right," "upper," "lower," "down," "up," "side," and the like are used in the written description for clarity in specific reference to the Figures and are not intended to limit the scope of the invention or the scope of what is claimed.

Aspects of the inventions disclosed herein may be embodied as an apparatus, system, method, or computer program product. Accordingly, specific embodiments may take the form of an entirely hardware embodiment, an entirely software embodiment or an embodiment combining software and hardware aspects, such as a "circuit," "module" or "system." Furthermore, embodiments of the present inventions may take the form of a computer program product embodied in one or more computer readable storage media having computer readable program code.

All ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by those skilled in the art, a range includes each individual member. Thus, for example, a group having 1-3 components refers to groups having 1, 2, or 3 components. Similarly, a group having 1-5 components refers to groups having 1, 2, 3, 4, or 5 components, and so forth.

Items, components, functions, or structures in this disclosure may be described or labeled as a "module" or "modules." For example, but not limitation, a module may be configured as a hardware circuit comprising custom VLSI circuits or gate arrays, off-the shelf semiconductors such as logic chips, transistors, or other discrete components. A module also may be implemented as programmable hardware devices such as field programmable gate arrays, programmable array logic, programmable logic devices, or the like. Modules also may be configured as software for execution by various types of processors. A module of executable code may comprise one or more physical or logical blocks of computer instructions that may be organized as an object, procedure, or function. The executables of a module need not be physically located together but may comprise disparate instructions stored in different locations that when joined logically together, comprise the module and achieve the stated purpose or function. A module of executable code may be a single instruction, or many instructions, and may even be distributed over several different code segments, among different programs, and across several memory devices. Similarly, data may be identified and illustrated herein within modules, and may be embodied in any suitable form and organized within any suitable type of data structure. The data may be collected as a single dataset or may be distributed over different locations including over different storage devices, and may exist, at least partially, merely as electronic signals on a system or network. Where a module or portions of a module are implemented in software, the software portions may be stored on one or more computer readable storage media.

When implementing one or more of the inventions disclosed herein, any combination of one or more computer readable storage media may be used. A computer readable storage medium may be, for example, but not limitation, an electronic, magnetic, optical, electromagnetic, infrared, or semiconductor system, apparatus, or device, or any suitable combination of the foregoing. More specific, but non-limiting, examples of the computer readable storage medium may include the following: a portable computer diskette, a hard disk, a random access memory (RAM), a read-only memory (ROM), an erasable programmable read-only memory (EPROM or Flash memory), a portable compact disc read-only memory (CD-ROM), a digital versatile disc (DVD), a Blu-ray disc, an optical storage device, a magnetic tape, a Bernoulli drive, a magnetic disk, a magnetic storage device, a punch card, integrated circuits, other digital processing apparatus memory devices, or any suitable combination of the foregoing, but would not include propagating signals. In the context of this disclosure, a computer readable storage medium may be any tangible medium that can contain or store a program for use by or in connection with an instruction execution system, apparatus, or device.

Algorithms and/or computer program code for carrying out operations of one or more of the present inventions may be written in any combination of one or more programming languages, including an object-oriented programming language such as Java, Python, C++ or the like and conventional procedural programming languages, such as the "C" programming language or similar programming languages. The program code may execute entirely on the user's computer, partly on the user's computer, partly on the user's computer and partly on a remote computer, or entirely on the remote computer or server. The remote computer may be connected to the user's computer through any type of network, including a local area network (LAN) or a wide area network (WAN), or the connection may be made to an exterior computer for example, through the Internet using an Internet Service Provider.

Reference throughout this disclosure to "one embodiment," "an embodiment," or similar language means that a particular feature, structure, or characteristic described in connection with the embodiment is included in at least one of the many possible embodiments of the present inventions. The terms "including," "comprising," "having," and variations thereof mean "including but not limited to" unless expressly specified otherwise. An enumerated listing of items does not imply that any or all the items are mutually exclusive and/or mutually inclusive, unless expressly specified otherwise. The terms "a," "an," and "the" also refer to "one or more" unless expressly specified otherwise.

Furthermore, the described features, structures, or characteristics of one embodiment may be combined in any suitable manner in one or more other embodiments. In the following description, numerous specific details are provided, such as examples of programming, software modules, user selections, network transactions, database queries, database structures, hardware modules, hardware circuits, hardware chips, etc., to provide a thorough understanding of embodiments of the disclosure. Those of skill in the art having the benefit of this disclosure will understand that the inventions may be practiced without one or more of the specific details, or with other methods, components, materials, and so forth. In other instances, well-known structures, materials, or operations are not shown or described in detail to avoid obscuring aspects of the disclosure.

Aspects of the present disclosure may be described below with reference to schematic flowchart diagrams and/or schematic block diagrams of methods, apparatuses, systems, and computer program products according to embodiments of the disclosure. It will be understood by those of skill in the art that each block of the schematic flowchart diagrams and/or schematic block diagrams, and combinations of blocks in the schematic flowchart diagrams and/or schematic block diagrams, may be implemented by computer program instructions. Such computer program instructions may be provided to a processor of a general-purpose computer, special purpose computer, or other programmable data processing apparatus to create a machine or device, such that the instructions, which execute via the processor of the computer or other programmable data processing apparatus, structurally configured to implement the functions/acts specified in the schematic flowchart diagrams and/or schematic block diagrams block or blocks. These computer program instructions also may be stored in a computer readable storage medium that can direct a computer, other programmable data processing apparatus, or other devices to function in a particular manner, such that the instructions stored in the computer readable storage medium produce an article of manufacture including instructions which implement the function/act specified in the schematic flowchart diagrams and/or schematic block diagrams block or blocks. The computer program instructions also may be loaded onto a computer, other programmable data processing apparatus, or other devices to cause a series of operational steps to be performed on the computer, other programmable apparatus or other devices to produce a computer implemented process such that the instructions that execute on the computer or other programmable apparatus provide processes for implementing the functions/acts specified in the flowchart and/or block diagram block or blocks.

The schematic flowchart diagrams and/or schematic block diagrams illustrate the architecture, functionality, and/or operation of possible apparatuses, systems, methods, and computer program products according to various embodiments of the present inventions. In this regard, each block in the schematic flowchart diagrams and/or schematic block diagrams may represent a module, segment, or portion of code, which comprises one or more executable instructions for implementing the specified logical function(s).

It also should be noted that, in some possible embodiments, the functions noted in the block may occur out of the order noted in the figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated figures.

Although various arrow types and line types may be employed in the flowchart and/or block diagrams, they do not limit the scope of the corresponding embodiments. Indeed, some arrows or other connectors may be used to indicate only the logical flow of the depicted embodiment. For example, but not limitation, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, may be implemented by special purpose hardware-based systems that perform the specified functions or acts, or combinations of special purpose hardware and computer instructions.

In some possible embodiments, the functions/actions/structures noted in the figures may occur out of the order noted in the block diagrams and/or operational illustrations. For example, two operations shown as occurring in succession, in fact, may be executed substantially concurrently or the operations may be executed in the reverse order, depending upon the functionality/acts/structure involved.

In general terms and as disclosed more fully herein, we have invented systems and methods having one or more sensors or sensor types that transduce anatomical events in and around the trachea to predict if a patient is likely to aspirate a foreign substance (e.g., bolus, bodily fluids, etc.) and/or to detect whether a patient has aspirated a foreign substance. See, for example, FIGS. 1A-1D, in which the neck region 102, trachea 104, esophagus 106, lumen of trachea 108, and sensor target area 110 are illustrated.

As an aspiration event is predicted or detected, the system preferably notifies the patient, care giver or clinician of the predicted or detected event so that such person may intervene to cause the foreign substance to be expelled, such as through coughing, to implement preventative or prophylactic measures, improved swallowing techniques and modalities. Prediction and detection may be supported by algorithmic analysis of sensor signals, data convolution and/or deconvolution, signal processing and/or statistical analysis.

Our inventions may be used as a screening tool for detecting swallowing difficulty in patients in a hospital or other setting. Our methods and systems device may screen for food and/or liquids entering the trachea, referred to herein as an aspiration event or aspirant. Our methods and components may be implemented in a range of settings, including Emergency Rooms, Intensive Care Units, post-operative care units, rehabilitation facilities, nursing homes and other locations where patients with potential dysphagia may require screening In hospitals, clinics and other medical facilities, the methods and systems may be deployed bedside or in an examination location. The sensor portion (e.g., the external sensor assembly discussed below) of the system may be deployed on the patient by attending staff, after which a position reference check may be made by the device to assess the correct positioning on the patient's anatomy, e.g., neck. Incorrect positioning may be alerted to the attending staff for corrective action.

Once properly placed, the method and system may be activated by the user (e.g., clinician), and a normal or standardized protocol of liquids and/or solids administered to the patient. The sensors will then transduce relative or absolute changes in sensor signals to detect or not detect the presence of aspirant in the trachea after the liquids and or solids are swallowed. The methods and systems may output or display this information to the attending staff. This information can be in digital, audio, haptic or other combinations of communication forms.

In some embodiments, the methods and systems may characterize the nature of the aspirant (e.g., liquid, solid, semi-solid, dry), its direction of travel, and/or its location within in the trachea. These characterizations can also be communicated to the user, whether clinician, caregiver, or patient.

When an aspiration event is predicted and/or detected by our inventions, the attending care giver may refer the patient for further evaluation and testing by other means to characterize the nature of the dysphagia and to assess treatment options. A record of the aspiration event(s) may be stored in the system, and/or a connected device, and/or transmitted to a remote location for archiving and further analysis by care givers or others. If no aspiration event is detected, the attending care giver may recommend that no further testing is warranted, and/or that the patient can eat normally.

Figure 3A:
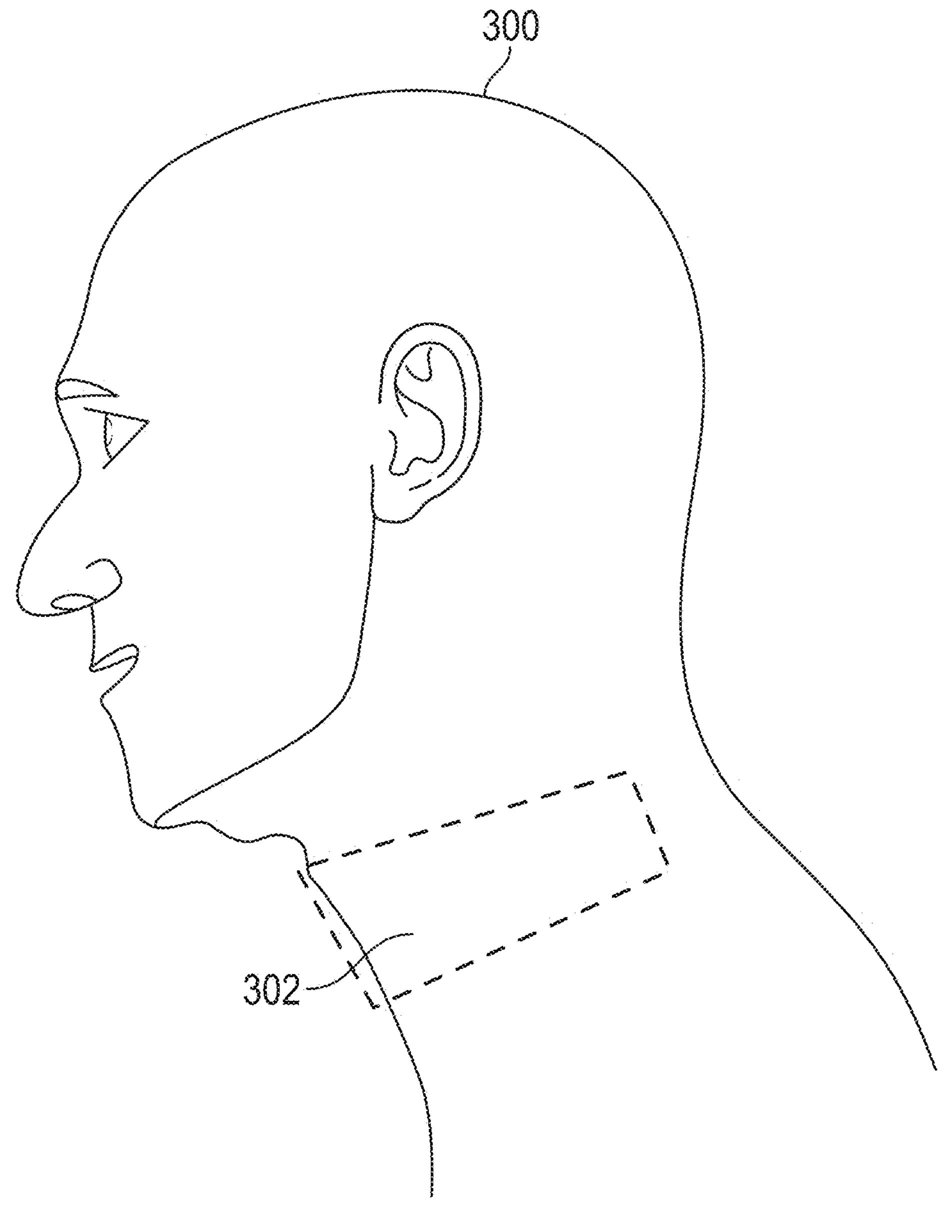
FIG. 3A illustrates a human neck region and preferred placement of an external sensor assembly.
Figure 3B:
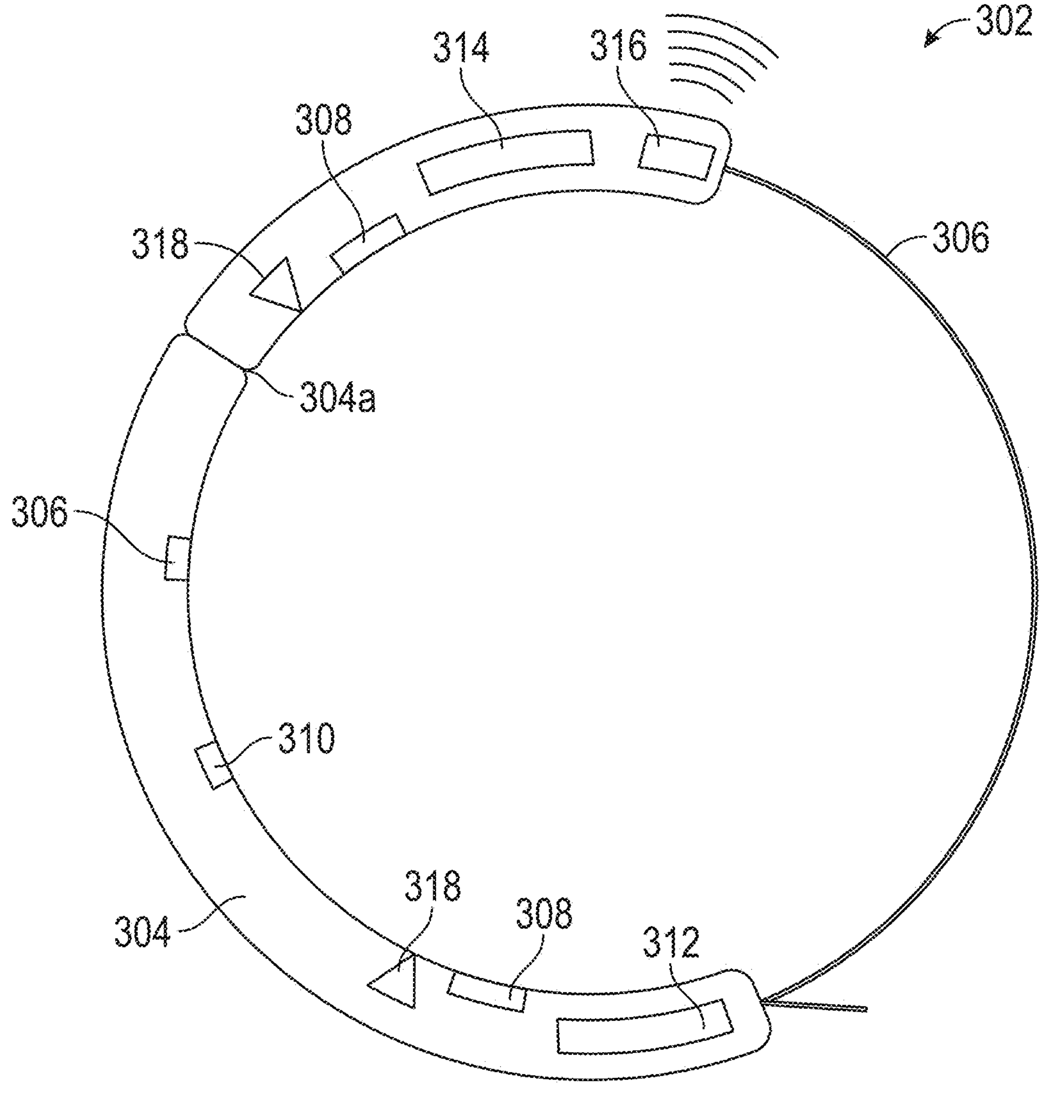
FIG. 3B illustrates one of many possible embodiments of an external sensor assembly.
Figure 3C:
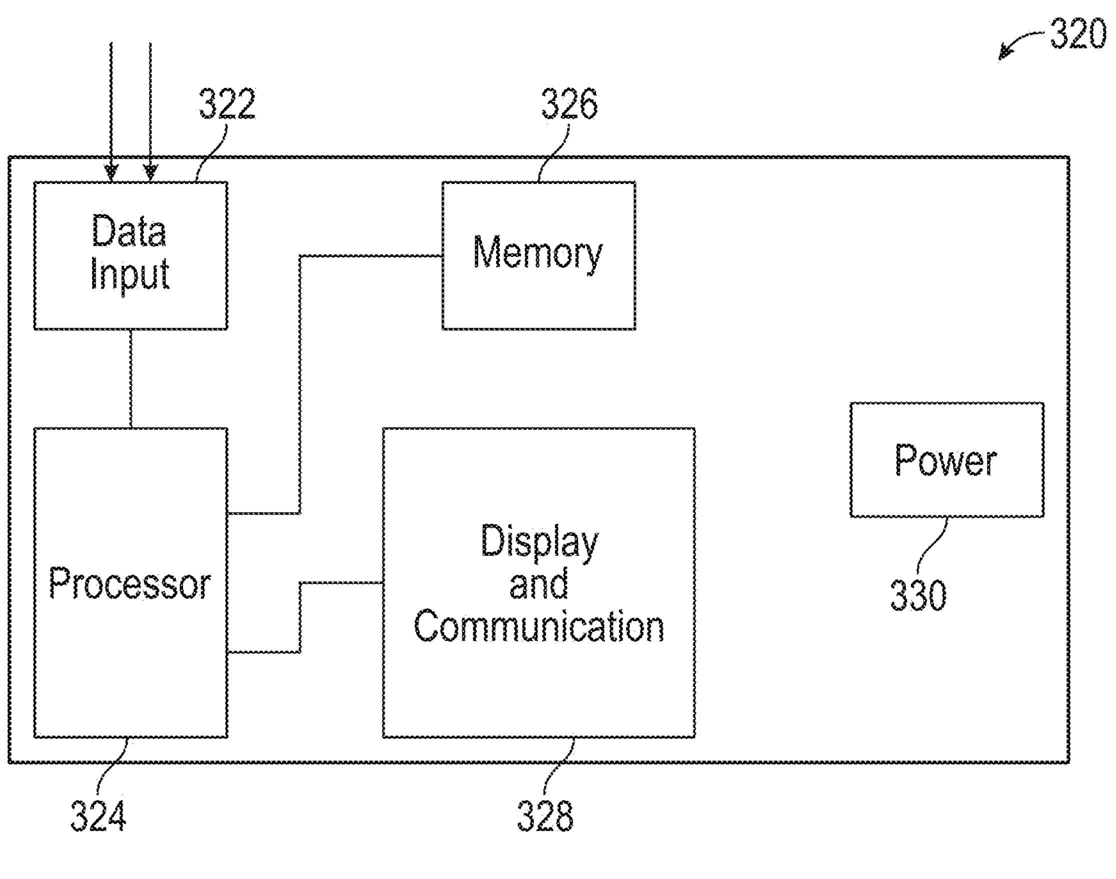
FIG. 3C illustrates a remote monitoring device for use with embodiments of the present inventions.

In the clinical setting, our inventions may be comprised of two functional assemblies: an external sensor assembly 304 and a display, control and processing assembly 320 (see FIGS. 3B and 3C). The external sensor assembly 304 may be deployed externally to the patient's neck in a manner that assures optimal signal transmission of sensor signals into and out of the anatomical areas being monitored. The sensor assembly 304 may be sterilizable for multiple uses, have disposable patient-contacting elements for a multiple-use sensor arrays, be sheathed in a disposable cover, or be completely disposable. The sensor assembly and/or individual sensors may be positioned on the patient's neck by means of a positioning strap 306, adhesives, mechanically through the form factor of the sensor device, by other external devices, or be applied manually by the attending care giver.

The display, control and processing assembly 320 may be mounted permanently in or adjacent to patient care locations, or on movable fixtures, such as medical carts. Communication between the sensor assembly and the control and processing assembly may be wired or wireless communication protocols or a combination of both.

In addition to clinical or diagnostic settings, our inventions are also applicable to outpatient use. For example, a stroke or cancer patient with dysphagia may use our inventions as a therapeutic tool to help prevent or minimize aspiration events. For example, before beginning a meal, the outpatient may apply a wearable, mobile version of our inventions to their neck area, such as external sensor assembly 304. The wearable system may communicate to the outpatient directly, such as through haptics or other physical interventions or may communicate, such as wirelessly, with a personal smart device, a dedicated system device, a smart device of a care giver, or a dedicated system device of a care giver 320.

Communication in whatever form serves to prompt the patient to cough or take other corrective action to mitigate the aspiration event. In addition, communication can inform the patient and/or care giver of substances and orientations in which the patient is more prone to aspirate, thus providing training in the effectiveness of prophylactic measures.

For outpatients, our inventions may allow them to eat with confidence, knowing that a true aspiration event will be detected, such that the outpatient can take appropriate action when needed. The form factor of the wearable sensor assembly 304 may be discrete, easily applied by the outpatient, or caregiver, and self-calibrating.

As discussed in more detail below, our inventions may employ one or more sensors, such as capacitive sensors, bio-impedance sensors, ultrasonic sensors, optical sensors (e.g., infrared sensors, terahertz (or far infrared) sensors, etc.), and/or acoustic sensors. It is contemplated that the one or more sensor(s) or sensor types employed may be selected based on, for example, the foreign substance to be detected, or on the anatomical event to be detected. For further example, and not for limitation, if it is desired to detect aspiration of foreign substances including saliva, bolus and dry substances, a system comprising an array of capacitive sensors and an array of ultrasonic sensors suitable aimed at and/or around the trachea may provide reliable aspirant detection. Further still, a system may comprise an array of capacitive sensors, an array of ultrasonic sensors, and an array of optical sensors (e g, infrared sensors) suitable aimed at the trachea for predicting and or detecting aspiration events.

Those persons of skill having this disclosure will appreciate that the external sensor assembly whether for clinic use or outpatient use may embody a simple system of one sensor type and one sensor (e.g., a combined transmitter/receiver) to complex systems having multiple sensor types and multiple sensors. In a clinic setting for example, the external sensor assembly may comprise all the sensor types listed above and may allow the clinician to selectively employ such sensors and sensors types as desired or required for the specific patient. In this type of embodiment, the clinician may utilize a single capacitive sensor element in one test, and next utilize multiple capacitive, ultrasonic and optical sensors in another test. In an outpatient setting, the external sensor assembly may comprise only those sensor types suitable for the patient's specific dysphagia issues.

As shown in the chart below, our investigations have shown that no one sensor type is best suited to detect all aspirant types. Of course, our comments of Best, Good and Worst are our relative conclusions and are not meant to state that a sensor modality cannot be used to detect the presence or absence of aspirant or bolus.

| Sensor Modality | Liquid | Semi-Dry | Dry |
|---|---|---|---|
| Capacitive | BEST | GOOD | WORST |
| Ultrasonic | WORST (Poor Sensitivity) | BEST | GOOD |
| Primary Infrared (Wavelength 845 nm) | WORST (Distilled Water) | BEST | BEST |
| Secondary Infrared (Wavelength 626, 635, 655 nm) | GOOD ≤0.2 ml Volume (2% Low Fat Milk) | BEST | BEST |
| Secondary Infrared (Wavelength 845 nm) | GOOD ≤0.2 ml Volume (2% Low Fat Milk) | BEST | BEST |
| Secondary Infrared (Wavelength 1200 nm) | WORST (Poor Sensitivity) | WORST (Poor Sensitivity) | WORST (Poor Sensitivity) |

In our investigations concerning optical (infrared) sensors, we were mindful of the average depth (transverse length) of the trachea from the front of the neck of about 13 mm and the tracheal diameter of about 20 mm Mid infrared (5,000 nm to 13,000 nm) was originally contemplated as the primary wavelength for an optical sensor but due to the 13 mm minimum offset it was concluded not to be feasible at body temperatures. Near infrared (835 nm to 940 nm) ultimately was selected as the primary wavelength. Clear liquids, such as water, have a minimum absorption at these wavelengths and are therefore not readily detectable using this modality. However, for bolus sizes greater than 15 mm, near infrared wavelengths returned 100% true positive, 0% false positive, 100% true negative, and 0% false negative (excluding liquid) in our investigations.

EXTERNAL SENSOR ASSEMBLIES. We turn now to more detailed descriptions of external sensor assemblies suitable for use with our inventions. With reference to FIGS. 3A-3C, external sensor assemblies 304 may comprise one or more or more discrete sensors of one or more sensor types (e.g., 308, 310) positioned and operated to transduce anatomical changes and/or bolus events to detect aspiration. The sensors are preferentially placed externally about the trachea in a variety of orientations depending on the type of sensor modality. For example, some sensor modalities may prefer placement radially about the trachea, while other sensors may perform better with both azimuthal and elevation angles about a co-targeted tracheal target point to optimize beam pattern, sensitivity, selectivity, and noise immunity. Sensor placement should optimize, where applicable, beam pattern, sensitivity, selectivity, noise immunity, and reduce sensor-to-sensor interference.

Figure 2A:
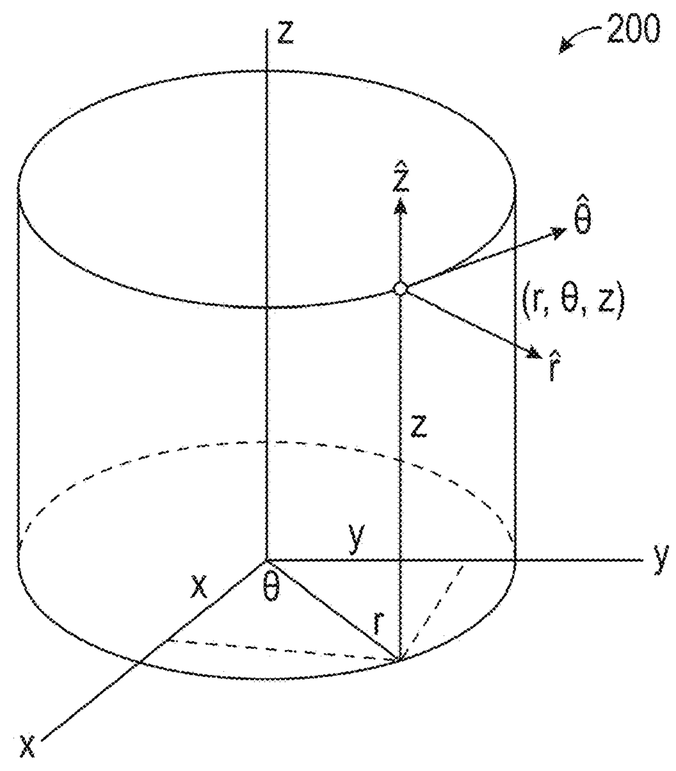
FIGS. 2A and 2B illustrate cylindrical and spherical coordinate systems useful with sensor placement for the subject inventions.
Figure 2B:
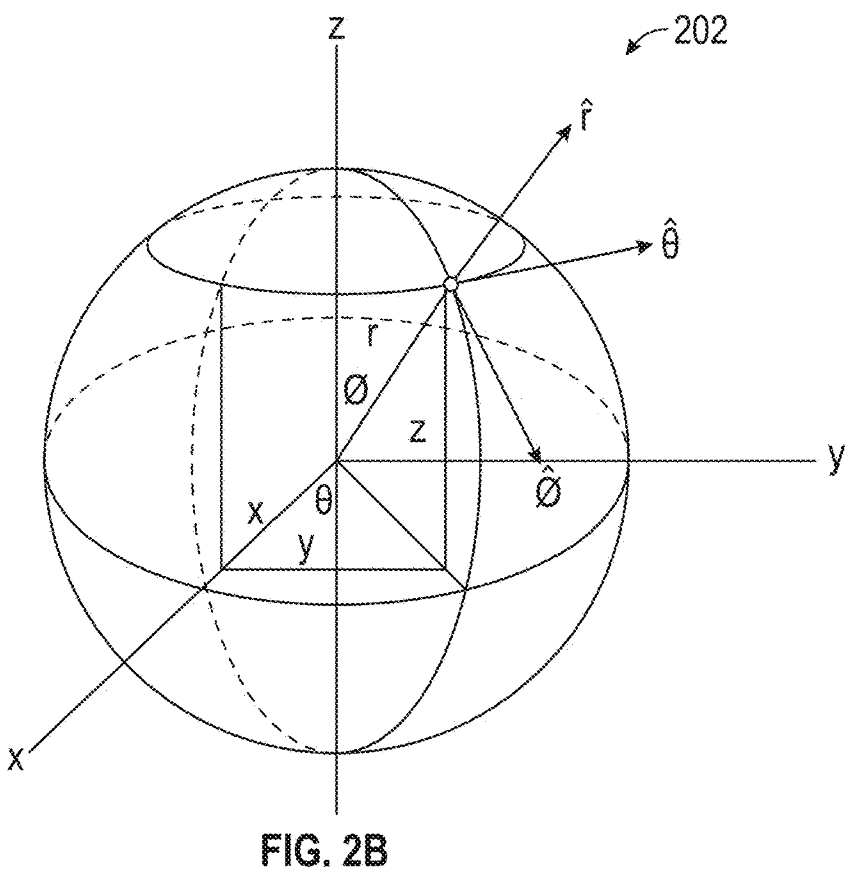
Figure 2C:
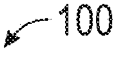
FIGS. 2C, 2D and 2E illustrate preferred sensor placement coordinates about a human neck
Figure 2C:
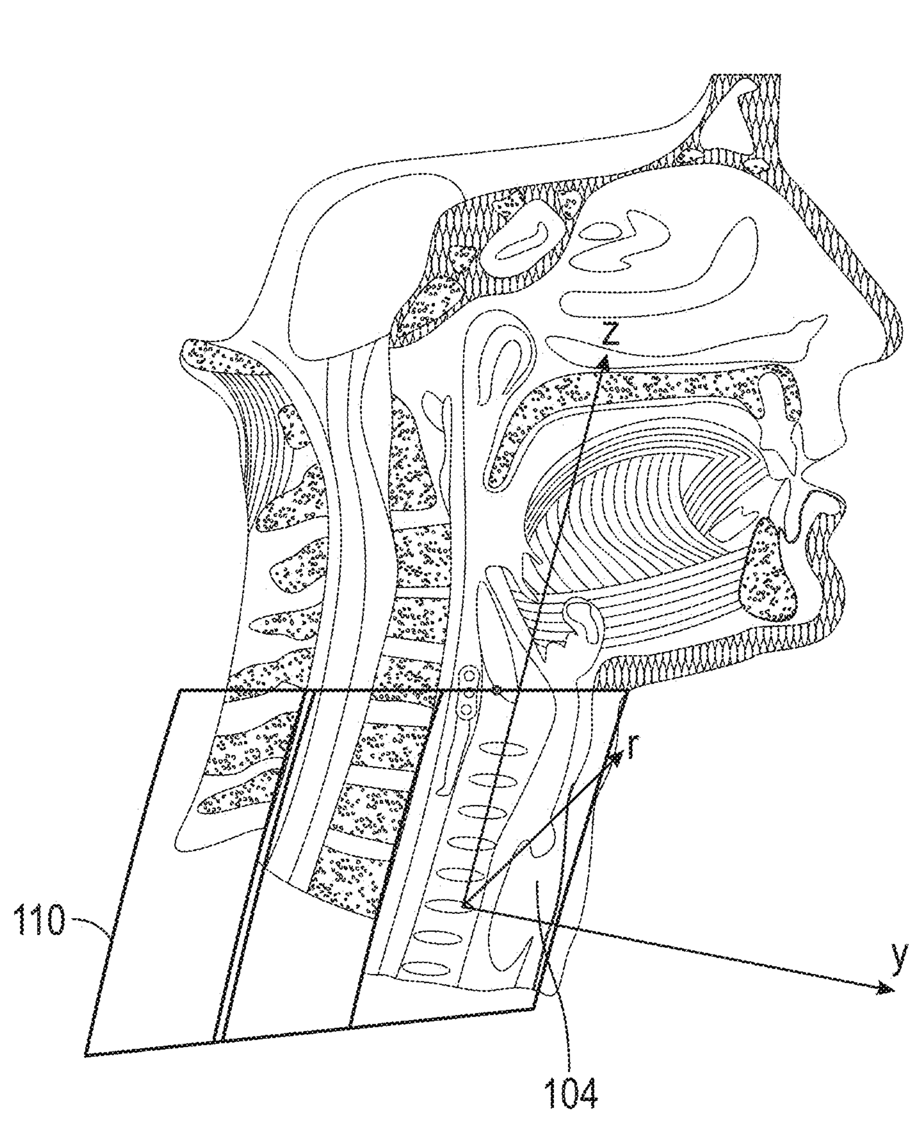
Figure 2D:
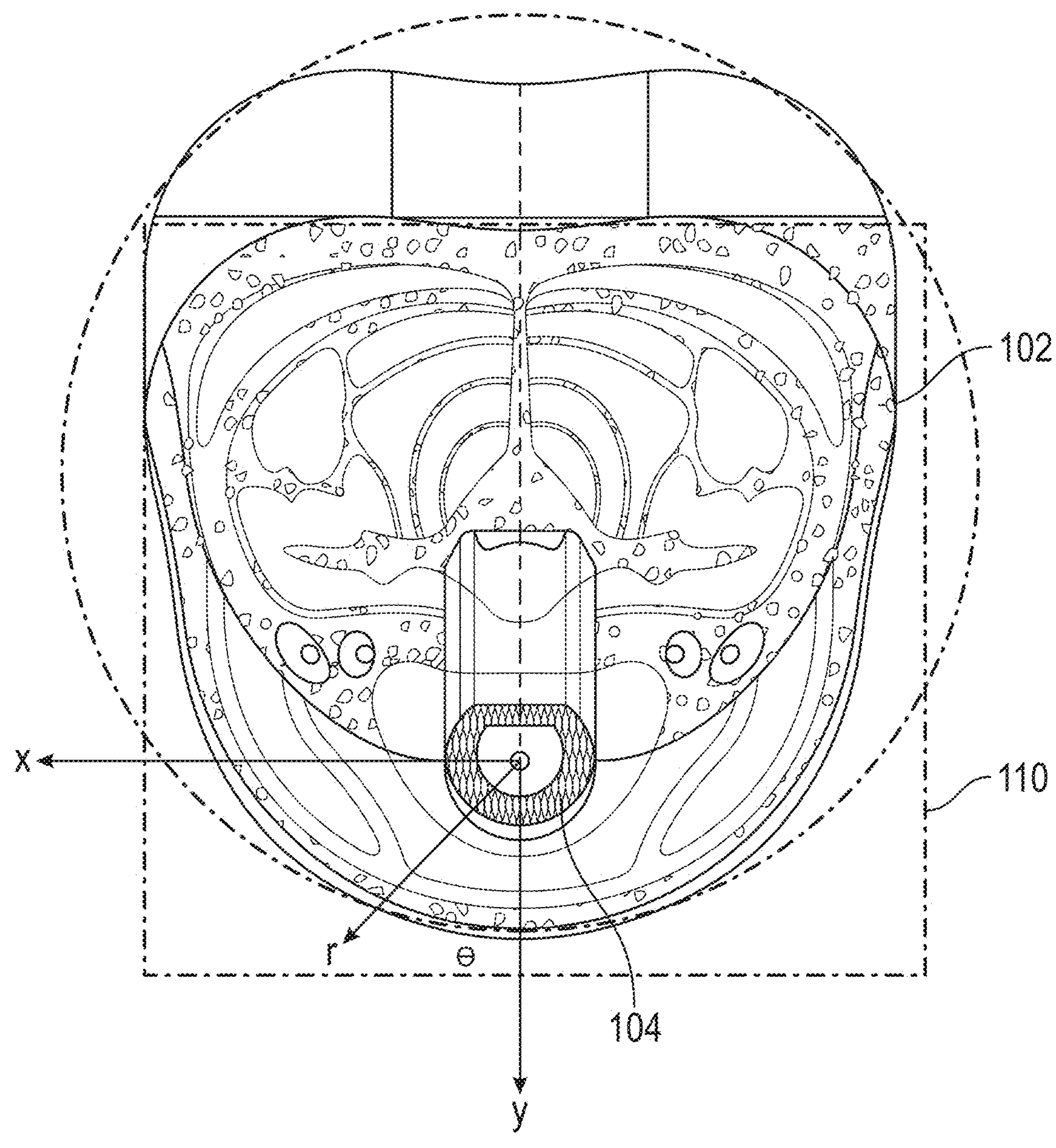
Figure 2E:
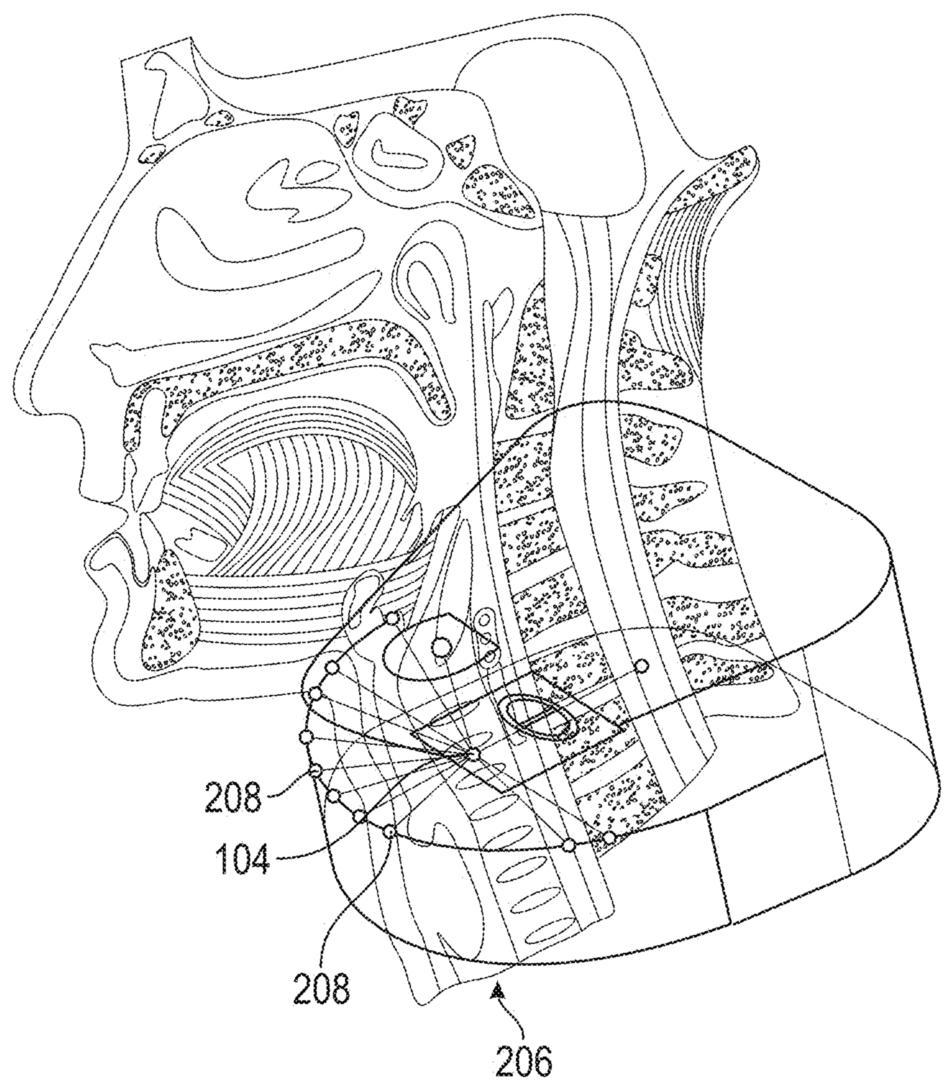

FIGS. 2A-2E illustrate coordinate systems relative to the neck region useful for positioning sensor(s) in the external sensor assembly 304. FIG. 2A illustrates a cylindrical coordinate system 200 that intuitively models the human neck region, whereas FIG. 2B illustrates a spherical coordinate system 202 that may better facilitate placement and orientation of multiple sensor types in an external sensor assembly. FIGS. 2C-2E illustrate coordinate systems applied about the trachea 104 in a preferred detection area 110. FIG. 2E also illustrates an external sensor assembly 206 having multiple sensors 208.

It is presently preferred, but in no way required, that external sensor assemblies be designed such that the sensor(s) can detect an anatomical landmark, such as the cricoid cartilage, or the assembly body 304 can be position relative to an anatomical landmark, such as the suprasternal notch (or Plender gap) to ensure and/or enhance the sensor detection region of the trachea. For example, in outpatient embodiments, an auto-calibrate algorithm may be employed to alert the patient to adjust placement of the external sensor assembly to maximize aspirant detection, sensitivity and specificity. Without limitation, in clinical settings the external sensor assembly may allow the clinician to visualize the cricoid cartilage or other anatomical structure to confirm or adjust placement as necessary or desired.

It is preferred, but not required, that the external sensor assembly be packaged into a wearable, collar-like device (e.g., 304), which may be easily attached and removed by the clinician, outpatient or caregiver. For clinical settings, it is preferred that the external sensor assembly comprise the sensors (e.g., 308, 310) for aspirant detection, but the related signal conditioning and processing electronic circuits, power source, and user interface including feedback upon detection (e.g., audible, visual, vibratory) be housed in a remote or tabletop processing device. In such embodiments, power for the sensors and data communication can be, and preferably is, achieved through wired connection between the external sensor assembly and the remote processing device. In such embodiments, the remote device would process the transduced data to indicate to the clinician the presence of an aspirated liquid or bolus, approximate volume (size) and/or type (liquid, semi-dry, or dry) of aspirant, transit time (mm/sec, mm/min, etc.) of the aspirant through the trachea.

FIG. 3C illustrates one such remote processing device 320 comprising a sensor data module 322 operative to receive sensor data and/or to communicate with or control the sensors; a logic processor 324 operative to implement algorithms and/or software to process the sensor data; volatile and/or non-volatile memory 326 for storing and accessing algorithms, software and data; a human interface module 328 having for example, visual and auditory outputs, such as images and sounds, to provide real time information to the clinician about actual and predicted aspiration event. The remote device 320 may also comprise a power source for its components as well as for the external sensor assembly.

For outpatient settings, it is preferred that the external sensor assembly (e.g., 304) comprise the sensors for aspirant detection, related signal conditioning and processing electronic circuits 314, a power source 312, and user interface including battery charge level, power on, and feedback upon detection 318 (e.g., audible, visual, vibratory, voice. Alternately, for outpatient settings, the user interface may be provided, such as wirelessly, to a remote monitor (e.g., an outpatient smart or a caregiver smart device). The remote device 320 illustrated in FIG. 3C may be a smart device such as a smartphone or tablet. In such embodiments, the external sensor assembly 304 also may comprise a wired, but preferably wireless, data link 316. It is preferred that in outpatient settings the external sensor assembly communicate via Bluetooth® or other short range wireless communication protocol to the remote device 320. As discussed elsewhere, the remote device 320 also may provide cellular connectivity to first responders.

Figure 4A:
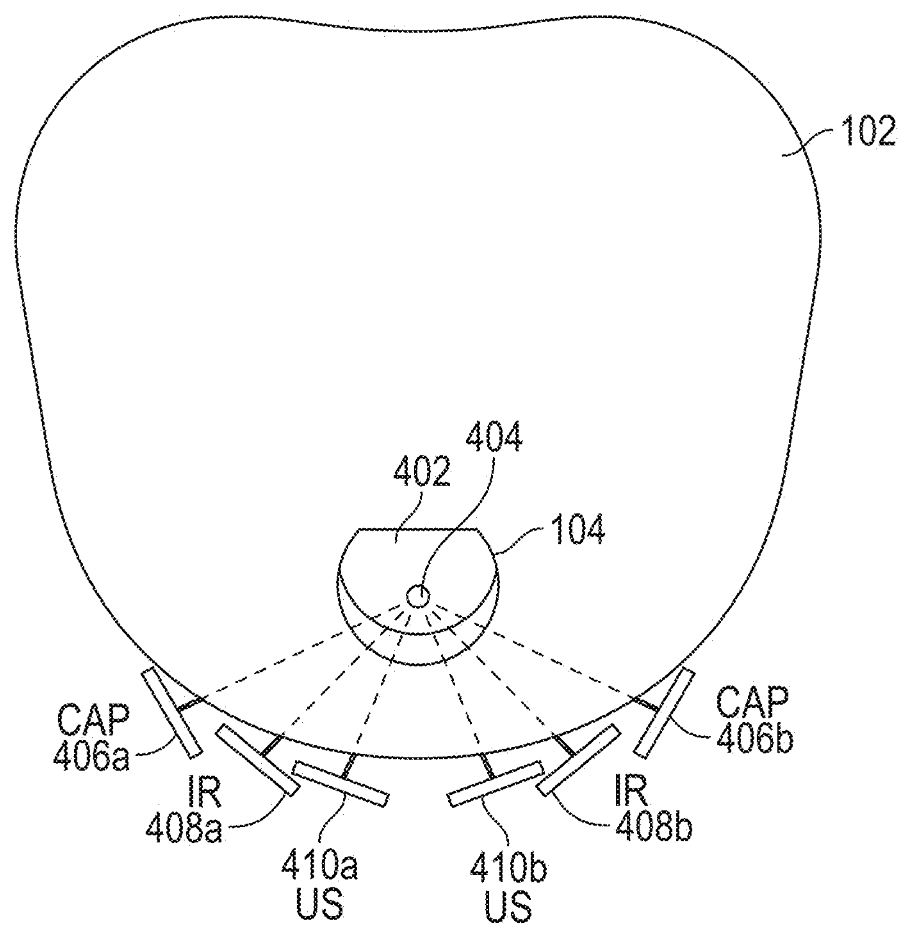
FIGS. 4A and 4B illustrate multiple sensor types focused on a point or region in the lumen of trachea and on a point or region outside of the lumen of trachea.
Figure 4B:
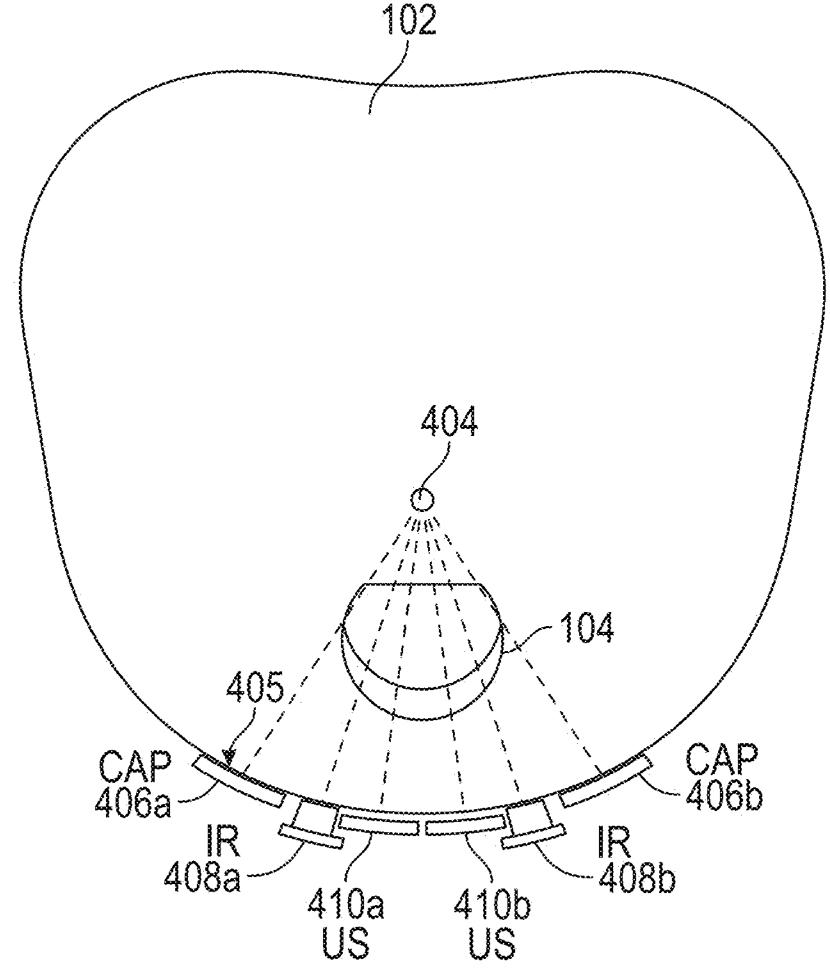

SENSOR MODALITIES OR TYPES: Our inventions may employ one or more sensors and from one or more sensor types to transduce, detect or measure one or more of: (i) anatomical characteristics, such as the throat or the hyoid bone; and (ii) aspirant/bolus characteristics, such as presence, amount, location, direction of travel, and/or density. FIGS. 4A and 4B illustrate a plurality of sensors (e.g., 406*a*, 406*b*) and sensor types (e.g., 406*a*, 408*a*, and 410*a*) in an external sensor assembly disposed about a human neck 102. In FIG. 4A, the sensors are configured in the external sensor assembly to focus their field of detection at effectively the center of the lumen of the trachea 402. FIG. 4B illustrates one of many possible alternatives in which the sensors are configured in the external sensor assembly to focus their field of detection at a location outside of, and posterior to, the lumen of the trachea 402. Those of skill will appreciate that external sensor assemblies may utilize sensors of the same type that have different detection focal points, for example, some within the lumen and others without. Similarly, external sensor assemblies may utilize sensors of different types that have different detection focal points, for example, some sensor types may focus within the lumen and sensor types may focus outside the lumen.

Capacitive Sensor(s). A first sensor type that may be implemented in embodiments of our inventions, such as in the external sensor assembly, are capacitive sensors, based on capacitive coupling, which can detect and measure conductive materials, such as human tissue, or material that has a dielectric constant different from air. The capacitance of the sensor(s) will increase with the permittivity of aspirant in the trachea. For example, free air has a relative permittivity of $\varepsilon r=1.0006$ and water has a relative permittivity of $\varepsilon r=80$.

The capacitance of a capacitive sensor may be generally defined as $C=\varepsilon\times A/d$ where C=Capacitance, ε=absolute total permittivity of the dielectric and the aspirant, A=area of plates, and d=distance between plates.

The dielectric properties, such as permittivity, of human tissue are well reported, including in, for example, C. Gabriel. Compilation of the Dielectric Properties of Body Tissues at RF and Microwave Frequencies, Report N.AL/OE-TR-1996-0037, Occupational and environmental health directorate, Radiofrequency Radiation Division, Brooks Air Force Base, Texas (USA), 1996, the contents of which are incorporated herein by reference. For example, the permittivity of the trachea at 1 kHz is reported to be 4.72E+4, and the permittivity of the trachea lumen is reported to be 1.00E+0. At 1 GHZ, the permittivity of the trachea at 1 KHz is reported to be 4.18E+1, and the permittivity of the trachea lumen is reported to be 1.00E+0.

Figure 5A:
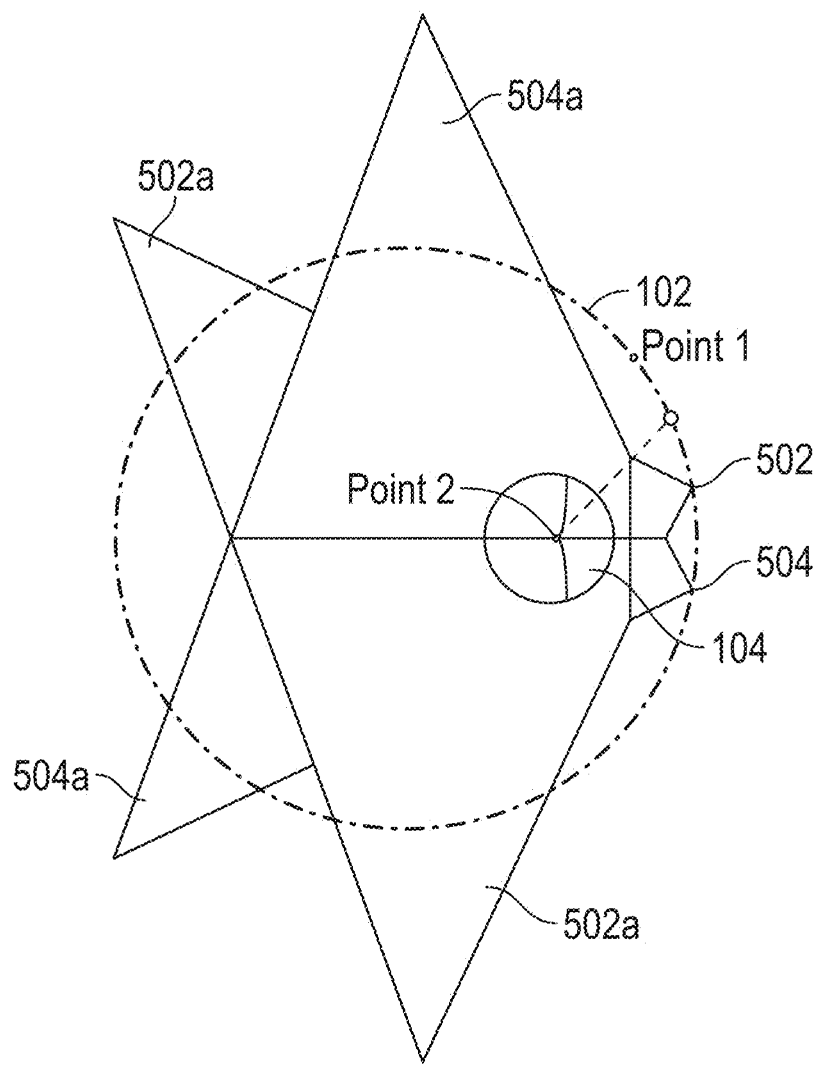
FIGS. 5A and 5B illustrate detection overlap of two capacitive sensors placed about the neck region to detect and/or predict aspiration.
Figure 5B:
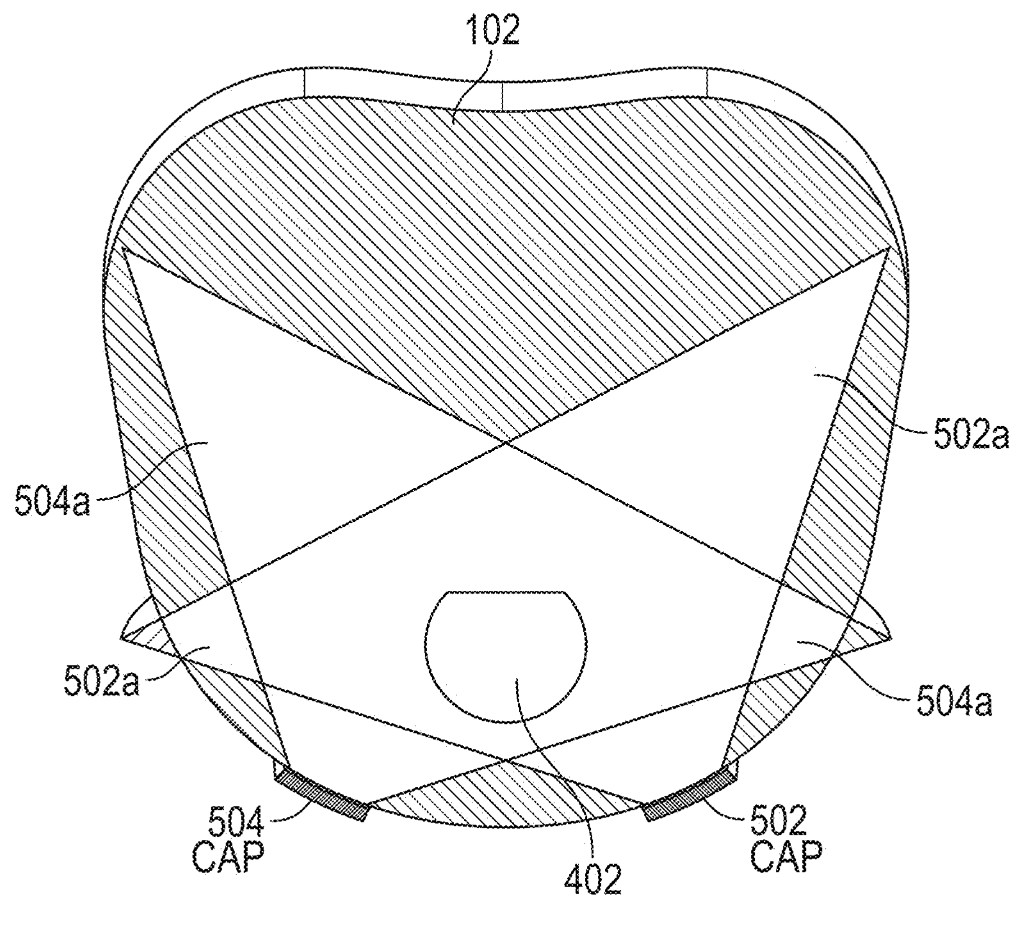

With reference to FIGS. 5A-4B, a capacitive sensor (e.g., 502, 504) useful with our inventions may comprise a single or multi-plate capacitive sensor, with an insulative layer between the capacitive sensor and tissue to minimize the conductive effects of skin and perspiration. A multi-plate capacitive sensor may minimize common-mode noise and maximize sensor coverage over an area or volume Regarding placement of capacitive sensor(s) according to our inventions, one or more capacitive sensor(s) 502, 504 may be placed radially about the neck 102 such that the sensor(s) "focuses" on the trachea lumen, the posterior wall of the trachea or other trachea volume. One or more capacitive sensor(s) or sensor arrays may be placed radially about the neck 102 at locations different from other capacitive sensors or sensor arrays to optimize the shape of the detectable electric field pattern (e.g., beam forming) Such beam forming placement may include different azimuthal angles, elevations, sensor geometry, and sensor proximity to the skin. Placing sensors or sensor arrays at different elevation angles may allow using their sequential outputs to monitor the bolus velocity, or direction of travel (e.g. from mouth to lungs or vice versa). The direction of travel may be used to confirm that the bolus was partially or fully ejected (or not) after intervention, such as patient coughing. Also, matching pairs of sensors or sensor arrays may be placed at symmetrical angles about the neck. FIGS. 5A and 5B illustrate capacitive detection fields for two capacitive sensors 502 and 504, with the fields being represented by 502*a* and 504*a* respectively. It is seen that these capacitive sensors sweep the entire trachea for aspirant detection purposes. Embodiments of our inventions are not limited to one or two capacitive sensors and may comprise three or more in a single external sensor assembly.

Fundamentally, our inventions comprise detecting a change in capacitance of the one or more capacitive sensors sensor arrays to indicate the presence of an aspirant in the detection area (e.g., trachea volume). In a basic form, we envision at least one capacitive receiver and one capacitive emitter pair. It is preferred that pairs of matching are utilized at electromagnetic frequencies that readily pass through human tissue with minimum attenuation, e.g., 3 kHz (HF) to 3 GHZ (UHF). The use of a plurality of capacitive sensors or arrays and related "capacitive signatures" may be used to identify the type of bolus.

In an analog mode with matching pair sensors, the coupled electromagnetic field amplitude received by the receiver is continuously proportional to the output of the emitter. Any bolus in the detection area in the path of the signal or field will change the measured capacitance. The bolus may block the emitted field or signal, reflect or redirect the emitted field or signal.

In a digital mode, the electromagnetic field amplitude received by the receiver may be compared to a threshold value and a high or low output generated that is proportional to the output of the emitter. Any bolus in the detection area in the path of the signal or field will be detected as a change in with respect to the threshold value. The bolus may block the emitted field or signal, reflect or redirect the emitted field or signal.

In other embodiments, the emitter output can be varied, such as varying the amplitude of the emitted signal, which may ensure adequate dynamic range and noise immunity. A varying emitter output can be used to establish an output signal of known amplitude when no aspirant is present.

Our inventions may comprise circuits incorporating the capacitive sensor(s) or arrays as the reactive element(s) within a low pass filter network driven by a constant frequency source such that as the capacitance of the sensor(s) or arrays change in the presence/absence of an aspirant, the instantaneous amplitude of the low pass filter network output changes accordingly. Alternately or additionally, the instantaneous phase shift (output versus input) of the low pass filter network may change as in the presence/absence of an aspirant.

If a constant frequency rectangular wave source is used, the rate at which the capacitor charges and discharges changes according to the presence/absence of aspirant. Slower rates of charge/discharge correlate with the presence of an aspirant.

Our inventions also comprise incorporating the capacitive sensor(s) as the reactive element(s) within a high pass filter network driven by a constant frequency source such that the capacitance of the sensor(s) change in the presence/absence of an aspirant, the instantaneous amplitude of the high pass filter network output changes accordingly, and/or the instantaneous phase shift (output versus input) of the high pass filter network output changes accordingly.

Our inventions also comprise incorporating the capacitive sensor(s) as the reactive element(s) within a coupling network driven by a constant frequency source such that as the capacitance of the sensor(s) change in the presence/absence of an aspirant, the instantaneous amplitude of the low pass filter network output changes accordingly.

Our inventions also comprise incorporating the capacitive sensor(s) as the reactive element(s) within an RC oscillator circuit, such that as the capacitance of the sensor(s) change in the presence/absence of an aspirant, the instantaneous frequency of the RC oscillator's output changes accordingly and/or the instantaneous frequency of the RC oscillator's output changes accordingly where the oscillator output frequency is proportional to the sensor's instantaneous capacitance. The frequency output of the RC oscillator may be further coupled to a Phase Lock Loop (PLL) to convert the frequency proportional to changes in capacitance to a proportional output voltage. This may be done using the PLL's loop filter's output voltage to demodulate the PLL's input frequency, which is proportional to frequency.

The capacitive sensor(s) circuit may use active-low circuit outputs to increase signal-to-noise ratio, minimize the effects of extraneous noise sources, and improve overall robustness of the capacitive sensor(s) detection system. Spatial filtering may be used to identify the location (region) of the bolus within the trachea. Further, sensor fusion techniques may be used to further improve the sensitivity and specificity of the capacitive sensor system, and identification of capacitive "sensor signatures" to better identify the type of bolus.

Ultrasonic Sensor(s). In their basic form, ultrasonic sensors measure distance by emitting and receiving ultrasonic sound (i.e., pressure waves). The sensor emitter emits an ultrasonic wave (e.g., 20 kHz to about 800 MHZ) and receives the wave reflected by the target. Ultrasonic sensors measure can distance to the target by measuring the time between the emission and reception. Of course, the speed of sound is a function of the medium through which the sound travels. Sound through air has a speed of about 344 meters per second at 20° C. The speed of sound in various human tissues has been studied and is known to those persons of skill in the art. For example, it is reported that the speed of sound in tracheal tissue is, on average, about 1,640 m/s, and the speed of sound through the trachea lumen is, on average, about 343 m/s. For tissues with unknown or unsubstantiated values, we propose assigning a value of 1,500 m/s. Ultrasonic sensors also can be used to detect changes in the medium through which they travel. In other words, the time for sound wave to be reflected from a known target will be a function of the media through which the sound travels. Bolus in the trachea can be detected in this manner by ultrasonic sensors.

In addition to or in place of a capacitive sensor or sensor array, our inventions may comprise an external sensor assembly having single or multi-element ultrasonic sensor(s) to maximize the detected or covered area or trachea volume. Embodiments may utilize a semi-solid layer between the ultrasonic sensor and tissue to provide optimal acoustic impedance matching between the sensor and tissue.

Figure 6A:
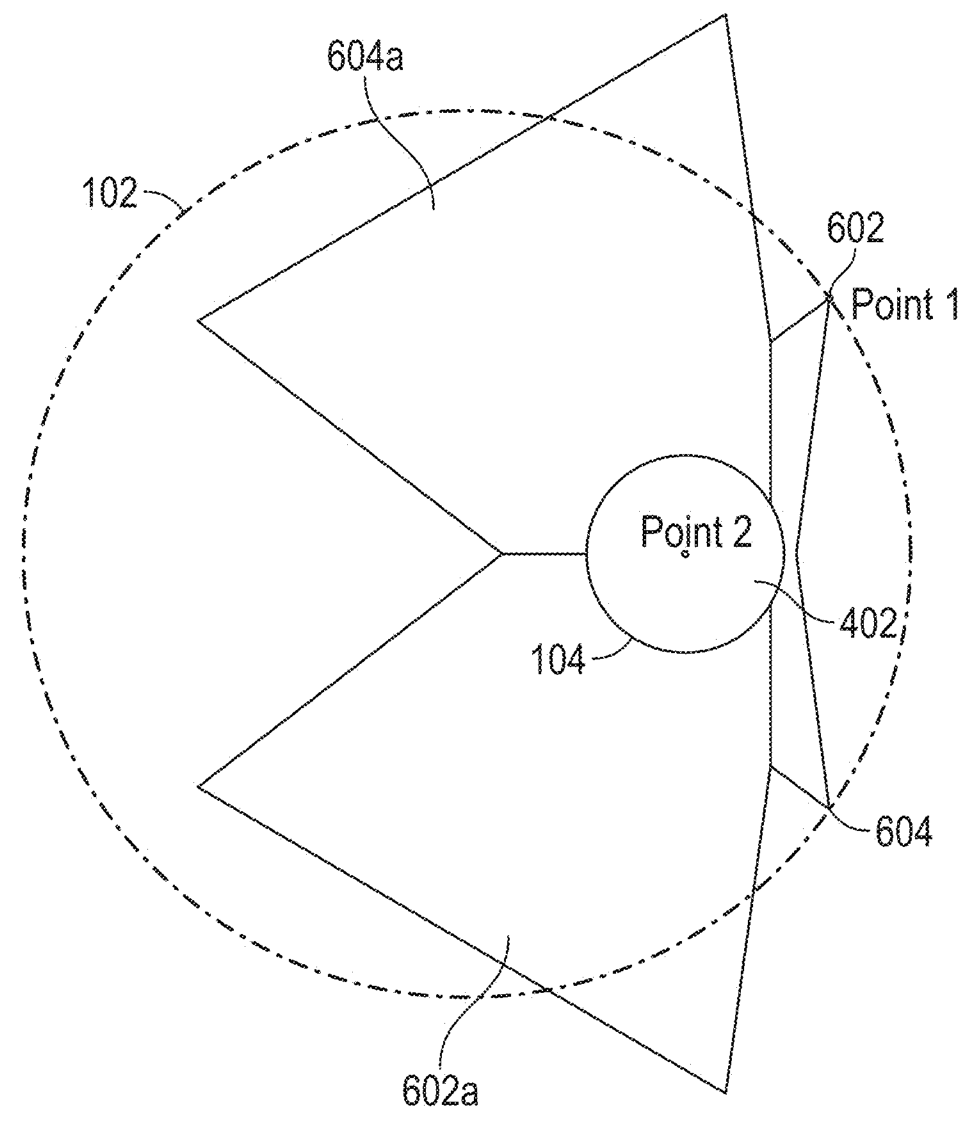
FIGS. 6A and 6B illustrate detection overlap of two ultrasonic sensors placed about the neck region to detect and/or predict aspiration.
Figure 6B:
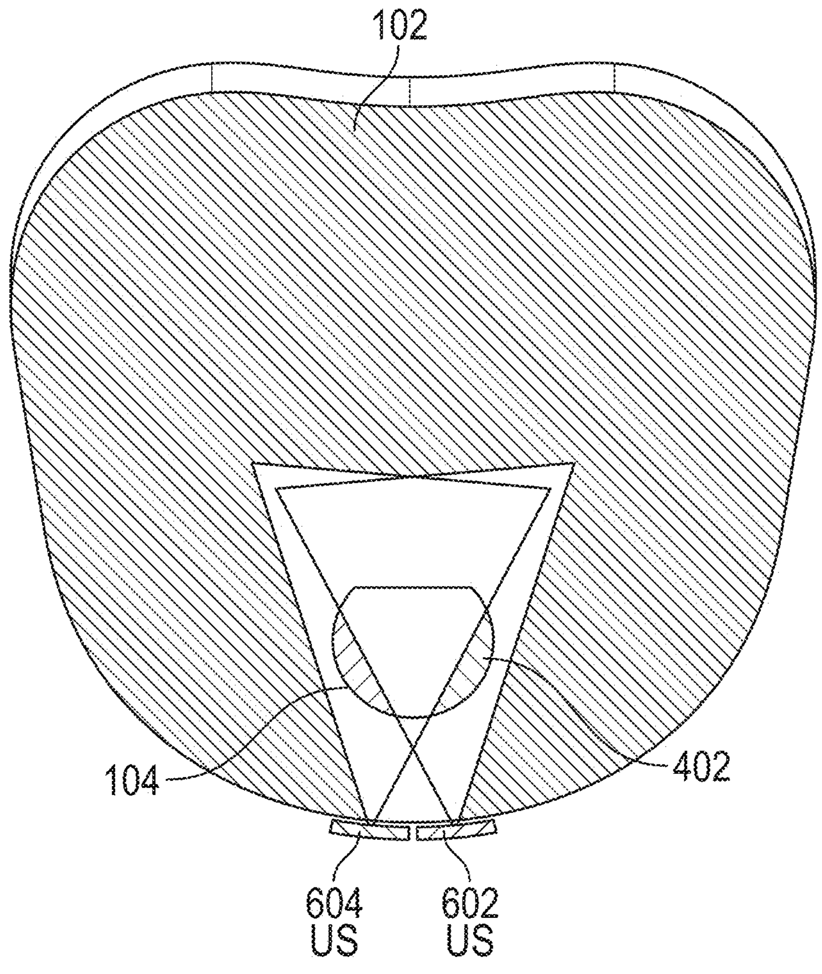

It is preferred that the ultrasonic sensor(s) be located radially about the neck such that they are "focused" on the trachea, such as described above for capacitive sensor(s). The placement of the ultrasonic sensor(s) about the neck can be optimized, such as by adjusting the shape of the detectable pattern (e.g., beam forming); the azimuthal placement and/or elevational placement of the ultrasonic sensors or sensor arrays can be optimized; the sensor geometry (e.g. disc, square, and/or rectangle) can be adjusted; the proximity of the sensor(s) to the skin; and/or using ultrasonic wave guide(s) (e.g. machined or molded acrylic sensor mount). FIGS. 6A and 6B illustrate ultrasonic sensor detection fields for two ultrasonic sensors 602 and 604, with the fields being represented by 602*a* and 604*a* respectively. It is seen that these ultrasonic sensors are oriented and coupled to the neck region to sweep the entire trachea for aspirant detection purposes. Embodiments of our inventions are not limited to one or two ultrasonic sensors and may comprise three or more in a single external sensor assembly.

For example, an external sensor assembly may comprise at least one ultrasonic receiver and one emitter pair, such that a detected change in transit time from when an outbound ultrasonic signal is emitted/transmitted by one ultrasonic element until it is received back to the same element may indicate the presence of an aspirant in the detection zone. Alternately or additionally, when a plurality of ultrasonic elements is employed, detection of a change in transit-time from when an outbound ultrasonic signal is transmitted by one ultrasonic element until it is received by different ultrasonic element may indicate the presence of an aspirant in the ultrasonic detection area. We contemplate that for external sensor assemblies that have multiple ultrasonic transmitting/receiving element pairs, the transmitting receiving pairs can alternate transmitting and receiving to conserve power and/or increase aspirant detection. A change in frequency between the transmitted signal and the received signal may be used to detect the presence of aspirant.

It is preferred, but not required that, a plurality of ultrasonic pairs that use different frequencies that readily pass through human tissue with minimum attenuation, such as 1 MHz, 2 MHz, and 5 MHz. Such matching pair sensors may be operated in an analog mode where the amplitude of the ultrasound signal received by the receiver is continuously proportional to the output of the emitter. Any bolus or aspirant in the detection zone may block or attenuate the ultrasonic energy emanating from the emitter or may reflect or redirect said ultrasonic energy emanating from the emitter.

Alternately, such matching pair sensors may be operated in a digital mode in which the amplitude of the ultrasonic signal at the receiver is compared to a threshold value, such as for a detection zone free of aspirant. A digital high or low output may be generated based on comparison to the threshold value to indicate the presence or absence of aspirant.

Our inventions also contemplate locating matching pairs of ultrasonic elements at symmetric angles from one another, and/or locating matching pair at asymmetric angles from one another, with the external sensor assembly. Our inventions also include, but do not require, the use of multiple ultrasonic emitters per receiver element.

The placement of the ultrasonic sensor(s) about the neck can be modified to optimize the shape of the detectable pattern (e.g., beam forming) For example, the azimuthal placement and/or elevational placement of the ultrasonic sensors or sensor arrays can be optimized, the sensor geometry (e.g., disc, square, rectangle), proximity to the skin, use of ultrasonic wave guide (e.g., machined or molded acrylic sensor mount).

When an ultrasonic signal is transmitted by one ultrasonic element the signal will encounter the tissue, muscles and spaces of the neck. The ultrasonic signal may pass through such anatomical structures, may be attenuated or blocked, and/or may be reflected or redirected. The ultrasonic signal, including as modified by the anatomical structures, may be received back to the same ultrasonic element. A change in transit time of the signal (emitted to received) may be used to indicate or detect the presence of an aspirant in the trachea. Similarly, a change in signal transit time from emittance to reception by another ultrasonic element (i.e., other than the emitting element) may be used to indicate or detect the presence of an aspirant in the trachea. It is contemplated that some embodiments of our inventions may employ alternately transmitting and receiving ultrasonic signals from multiple elements.

An ultrasonic signal of a given frequency (or range of frequencies) that passes through anatomical structures may experience a change in or modification of the signal frequency. This frequency change may be used to detect the presence or absence of aspirants. For example, a change in frequency of an ultrasonic signal transmitted by one ultrasonic element and received by another element may be used to detect the presence of an aspirant. It is preferred, but not required that embodiments of our inventions employ ultrasonic elements operating at frequencies that readily pass through human tissue with minimum attenuation, such as ultrasonic signals having a frequency of, for example, 1 MHz, 2 MHZ, and/or 5 MHz. Our inventions contemplate using at least one ultrasonic receiver and one ultrasonic emitter pair, using a plurality of matching pairs ultrasonic elements, and/or using multiple ultrasonic emitters per receiver.

Ultrasonic elements may be operated in an analog mode or a digital mode. In an analog mode, amplitude of the ultrasonic signal may be received by an element the receiver that is continuously proportional to the signal transmitted by the emitter. Any aspirant or bolus in the trachea will affect the amplitude of the ultrasonic energy emanating from the emitter. The signal may be blocked, or it may be reflected or redirected, thereby affecting or modifying the amplitude of the ultrasonic signal received by the element.

In a digital mode of operation, the amplitude of the ultrasonic signal received by the receiving element may be compared to a threshold amplitude value and a digital output indicative of that comparison may be generated. For example, a high or low output may be generated that is proportional to the threshold value and any bolus blocking, reflecting or redirecting the ultrasonic signal.

When utilizing matching pair elements, it may benefit aspirant detection to locate the matching pair elements at symmetric angles one from another. Alternately, it may be beneficial to locate the matching pair elements at asymmetric angles one from another. In addition, the emitter elements may have the same or differing beam angles.

For external sensor assemblies that employ ultrasonic sensors, it may be beneficial to locate an ultrasonic sensor at 0 degrees (i.e., directly in front of neck) to detect the posterior wall (back wall) of the trachea to nullify or minimize detection of bolus in the esophagus. Similarly, a plurality of ultrasonic sensors to detect the posterior wall (back wall) of the trachea and the overall circumferential boundary of the trachea to nullify or eliminate detection of bolus in the esophagus.

Spatial filtering (such as, beam forming) techniques may be used to, for example, identify the location (region) of the bolus within the trachea. Spatial filtering along with strategic geometric placement of emitters and detectors, such as azimuthally about the neck, or elevationally about the neck may aid aspirant location detection, which information may be used by the patient to expel the aspirant from the trachea. Similarly, selection of emitter beam angles, selection of receive beam angles, modulating the ultrasound energy of each emitter may be used to completely illuminate or wash the tracheal cross-section. Our inventions contemplate identification of "ultrasonic signatures" to help identify the type of bolus in the trachea, such as liquid, solid, or semi-solid.

Electromagnetic Sensors. Electromagnetic sensors, such as infrared sensors, are useful with embodiments of our inventions. Infrared sensors operate, in general terms, by emitting electromagnetic radiation (energy) in the infrared band, which energy has wavelengths longer than visible light, typically in the 780 nm to 1 mm range. Terahertz radiation has wavelengths between about 1 mm and 0.1 mm, which is at the far end of infrared spectrum. Terahertz radiation lies within the transition between microwaves and far infrared. For purposes of this disclosure, terahertz radiation will be considered a form of infrared radiation. Infrared radiation sensors, including terahertz radiation sensors, may be used with embodiments of the present inventions to detect the presence, absence, and/or characteristics of aspirant in the trachea.

The emitted radiation is reflected in varying degrees by structures in its path, including anatomical structure. Infrared sensors can detect a wide range of physical properties, such as temperature, motion, and proximity As is known, as the wavelength of radiation de-creases, the potential resolution of smaller objects increases. In other words, shorter wavelengths can detect smaller objects compared to longer wavelengths. Also, human tissue can attenuate or block certain wavelengths of infrared energy. Thus, our inventions balance the size of bolus that can be detected and the attenuation of the infrared energy. As discussed above, it is presently preferred, but not required, that energy in the near infrared region that has wavelengths between about 835 nm to about 940 nm be employed as the primary optical sensor modality. Optionally, or additionally, other forms is of infrared radiation having shorter or longer wavelengths may be employed alone or secondarily to the primary near infrared radiation. For example, infrared LEDs that emit infrared may be used.

Like other sensors useful with our inventions, an optical sensor may comprise an emitter and a receiver. The emitter may be an LED such as discussed above, and the receiver may be a photodiode sensitive to the emitted infrared radiation. In basic terms, the receiver's resistance and output voltage change in proportion to the infrared energy received.

Our inventions may utilize a single optical sensor (e.g., a single infrared emitter and receiver) or may utilize multiple optical sensors of the same or different wavelengths. The optical sensor(s) may be placed in the external sensor assembly so that they are located radially about the neck such that the sensors are focused on the trachea and maximize sensor coverage area/volume. In some embodiments, a solid optical filter may be placed between the optical sensor(s), whether reflective, transmissive, or imaging, and tissue to provide optimal filtering of the desired wavelength(s) between sensor and tissue. The sensors, either reflective, transmissive, or imaging, may be placed so that they are focused diametrically through the trachea. For example, and without limitation, an optical emitter may be placed diametrically opposite an optical receiver/imager Infrared radiation may transit the trachea such that any optically opaque or quasi-opaque structures in the trachea (e.g., aspirant) obstruct the energy as received by the imager resulting in a videographic image of an object/structure that may reveal, for example, movement, size, and related characteristics of aspirant.

Figure 7A:
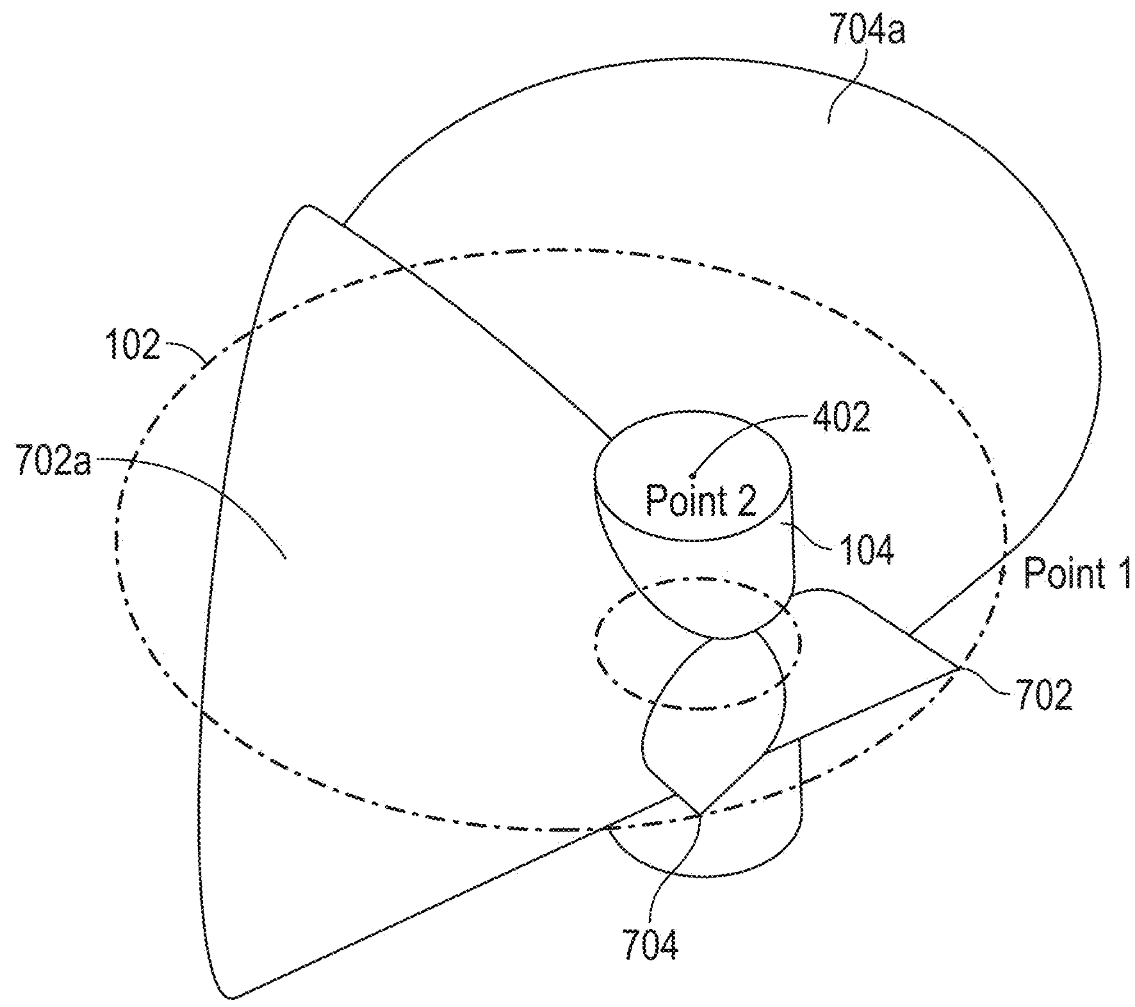
FIGS. 7A and 7B illustrate detection overlap of two infrared sensors placed about the neck region to detect and/or predict aspiration.
Figure 7B:
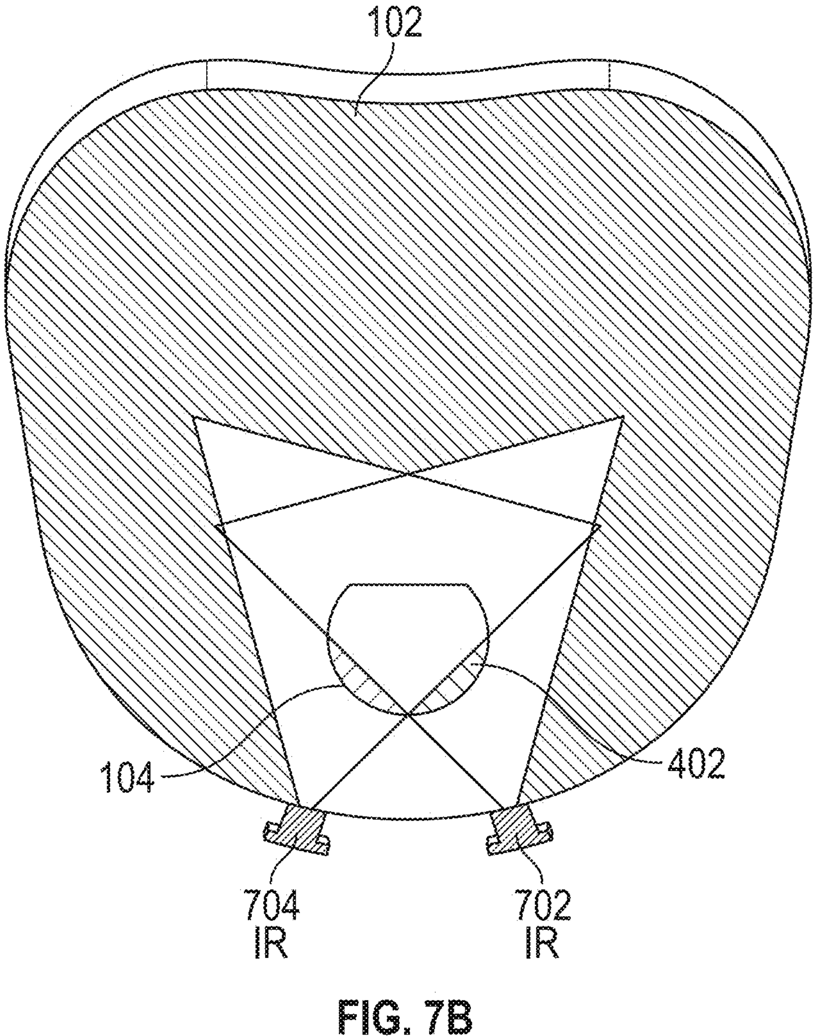

The placement of optical sensor(s) in the external sensor assembly are preferably placed radially about the neck (trachea) and may comprise different azimuthal and elevational angles related to a center of the trachea. Sensor geometry, such as shape, proximity of the emitter and/or receiver to the skin, use of an optical wave guide may be modified to optimize the shape of the detect-able radiation pattern. The optical sensors may be located at symmetric angles one from another, or at asymmetric angles one from another. As with other sensor modalities, the geometric placement of emitters and receivers azimuthally about the neck, geometric placement of emitters and receivers elevationally about the neck, selection of emitter beam angles, selection of receiver beam angles, and/or modulating the energy intensity of each emitter to completely illuminate the tracheal cross-section as viewed by the corresponding receiver, can be modified, optimized for individual outpatients or clinical settings. FIGS. 7A and 7B illustrate infrared sensor detection fields for two infrared sensors 702 and 704, with the fields being represented by 702*a* and 704*a* respectively. It is seen that these infrared sensors are oriented and coupled to the neck region to sweep the entire trachea for aspirant detection purposes. Embodiments of our inventions are not limited to one or two infrared sensors and may comprise three or more in a single external sensor assembly. In some embodiments, the infrared sensors may be replaced with terahertz sensors as described herein.

In addition, to infrared imaging, optical sensors can detect changes in reflected radiation absorption to indicate the presence (or absence of) aspirant. Alternately or additionally an infrared emitter may be associated with a plurality of infrared receivers and/or an infrared receiver may receive infrared energy from a plurality of emitters (i.e., not a paired emitter/receiver sensor) to detect changes in reflected radiation absorption. Changes in the frequency (or wavelength) of the received radiation may be used to indicate the presence or absence of aspirant.

In some embodiments, a plurality of optical sensors operating at two or more frequencies that readily pass through human tissue with minimum attenuation (e.g., 830 nm, 850 nm, 920 nm, 940 nm) may be employed in an external sensor assembly. When used in an analog mode, the amplitude of the infrared energy received by a sensor is continuously proportional to the infrared output of the emitter. Any aspirant that blocks, attenuates, reflects or redirects the infrared energy emitted by the sensor. When used in a digital mode, amplitude of the received infrared energy may be compared to a threshold amplitude value of a trachea with no aspirant. A digital output, such as a high and/or low signal, proportional to the comparison with the threshold value may be generated to indicate the presence or absence of aspirant.

In some embodiments, the emitter(s) may sweep a range of infrared frequencies and/or sweep a range of energy intensity over a period to aid the detection of aspirant and/or ensure adequate dynamic range and noise immunity. A change in energy scattering.

Unlike X-rays, terahertz energy (or rays) does not deliver damaging ionizing radiation but can "see" though or inside materials similarly to X-rays. Terahertz waves also have the potential to reveal the chemical composition of substances based on characteristic absorption patterns. Ultrasensitive terahertz wave detection using nonlinear optics may be used to image aspirants traversing the trachea. Some embodiments of our inventions using terahertz sensors may use a transverter to change the range of frequencies over which the sensor operates to discern absorption changes corresponding to various aspirants including thin liquid (e.g., water), thick liquid (e.g., apple sauce), semi-moist (e.g., pie), and dry (e.g., bread crust).

Because structures or particles, such as aspirant, cause infrared (light) waves to deviate from their straight path (i.e., light scattering). In other words, the presence of aspirant amy increase the scattering of infrared energy. Thus, in some embodiments, detection of energy scattering, or an increase in energy scattering, may be used to detect the presence of an aspirant. Additionally, detection of energy occultation, or an increase in energy occultation, may be used to detect the presence of an aspirant. A plurality of optical sensors may be used to create a library of "optical signatures" to better identify the type of aspirant/bolus.

Figure 8:
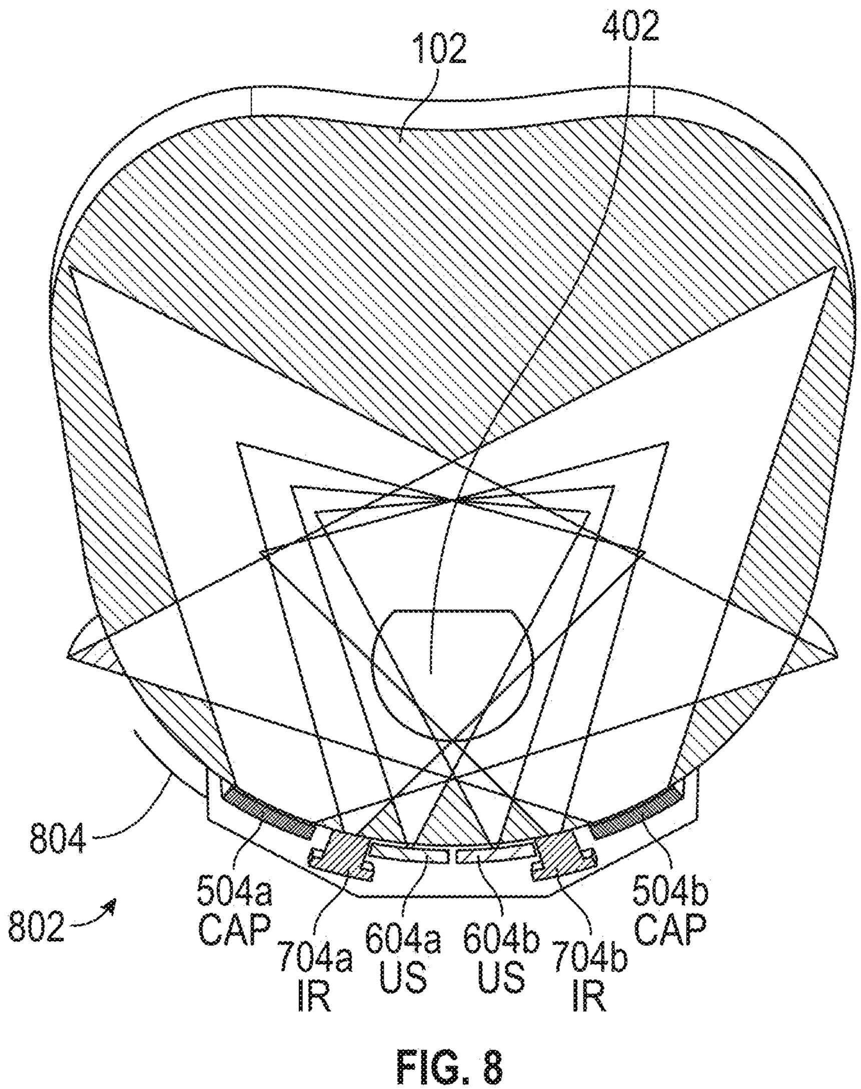
FIG. 8 illustrates detection overlap of a plurality of sensors and sensor types placed about the neck region to detect and/or predict aspiration.

FIG. 8 illustrates an external sensor assembly 802 comprising two capacitive sensors 502, 504, two ultrasonic sensors 602, 604, and two infrared sensors 702, 704 arranged generally transversely. The sensors are oriented and coupled to the neck region by the external sensor assembly to create the complex detection field that illuminates the entirety of the trachea region under investigation for the presence of aspirant. The external sensor assembly is preferably held in place by strap 804, which encircles the neck. 102. As discussed herein, depending on whether the external sensor assembly 802 is to be used by an outpatient or in a clinical setting, other components of the system for detecting or predicting aspiration may be housed in the assembly 802. FIG. 9A illustrates a capacitive sensor 902, an ultrasound sensor 906, and an infrared sensor 904 arranged generally vertically in an external sensor assembly. FIGS. 9B-9C illustrates the field of detection relative to the trachea for each of these sensors. Those of skill will appreciate that embodiments of our inventions may comprise sensors of the same or different types arranged both generally transversely and generally vertically in a single external sensor assembly to provide the best illumination of the trachea and, therefore, enhanced detection or prediction of aspiration.

Electromyographic Sensors. Electromyography is a biofeedback tool that uses small sensors that transduce muscle electrical activity, such as duration and amplitude, and has been used to evaluate dysphagia due to muscular insufficiency, but not necessarily detect the presence of aspirant in the trachea. Some embodiments of our inventions, especially those for use in clinical settings, may employ one or more single or multi-plate electromyographic sensors placed radially about the neck to optimize muscle signal acquisition. If multiple sensors are used, their placement may be organized in the external sensor assembly with respect to azimuth and elevation, and proximity to skin to optimize the detectable electromuscular field pattern. The system may be organized and operated to detect a change in electromuscular voltage potential to indicate the likelihood or imminence of aspiration and/or to predict and/or aspiration event. Those persons of skill will appreciate that such sensor may be oriented and coupled to the neck region via an external sensor assembly as described and illustrated in FIGS. 5A-9D.

Regardless of the number or type of sensors employed in the external sensor assembly, and whether for use in a clinical setting or for an outpatient, electrical will be needed for the sensors, for signal processing and for commination. Referring again to FIGS. 3A-3C, in clinical settings the external sensor assembly may be, and preferably is, powered, either wired or rechargeable, from a tabletop or medical cart based system. In outpatient settings, it is preferred that the external sensor assembly comprise its own mobile power source, such as replaceable or rechargeable battery or batteries. In such embodiments, it may be useful to implement one or more power saving functionalities, such as a human body detection mechanism (e.g., capacitance) to turn on or energize the external sensor assembly when placed on the human body and to turn off, deenergize, or enter sleep mode when the external sensor assembly is removed from the human body. Additionally, and depending on the type of sensor implemented, periodic on/off cycling of one or more of the sensor modalities may benefit power conservation. For example, making periodic infrared measurement(s) rather than continuous infrared measurements may be used to conserve power and/or sensor life. Although these power saving strategies may be most useful in mobile, outpatient external sensor assembly, such power strategies may be implemented in clinical setting systems as well.

Our inventions preferably utilize sensor signal processing circuits 314, 324 and algorithms to improve the sensitivity, signal-to-noise ratio, and specificity (as it relates to aspirant prediction or detection) of the transduced signals. Signal processing, including filtering, may be used to weight the sensor signals for different sensor modalities to improve system performance. Algorithms may utilize a voting system, algorithmic filters, such as Kalman filters, neural network, or artificial intelligence to optimize prediction and/or detection of aspiration events. In preferred embodiments, the systems comprise a logic-based controller that controls the external sensor assembly, such as operating or energizing one or more of the sensor modalities in a continuous or periodic manner, sampling the sensor(s) outputs, processing the sensor signals though circuits, algorithms or a combination of both, and reporting the results of the sensor detections. The controller 324 may implement time-division sampling of each sensor modality output, or equal-time sequential sampling, or non-equal-time sequential sampling of each sensor(s) output to maximize a particular sensor modality's temporal sensitivity.

As discussed above, in outpatient embodiments it is preferred that the controller, logic circuits, and algorithms reside in the external sensor assembly. Alternately, a smart device or dedicated remote device may contain the controller, logic circuits, and algorithms. In such embodiments, the external sensor assembly may communicate the sensor signals to the remote device. While digital communication protocols, such as Bluetooth®, may facilitate transmission of such signals, digital latency may suggest the use of analog communication protocols to achieve near real time transmission.

For clinical settings, it is preferred that the external sensor assembly does not contain the controller, logic circuits, and algorithms. Instead, it is preferred, but not required that a remote device, such as a monitoring station or dedicated processor, be wired to the external sensor assembly and contain the controller, logic circuits, and algorithms.

Alternately or additionally, the system, whether outpatient or clinical, may communicate wirelessly including cellular networks, to local first responders of one or more aspiration events, such as when an outpatient is alone.

Our inventions contemplate the use of an audible enunciator to alert the clinician, patient or caregiver of an aspirant detection and whose loudness may progressively increase until acknowledged by the user, such as by depressing a small switch on the external sensor assembly, a switch on a smart device, or a switch on monitoring station. Alternately or additionally, tactile information in the form of haptics (e.g., the use of an eccentric motorized mass) may be communicated to alert the clinician, patient or caregiver of an aspirant detection and whose intensity may progressively increase until acknowledged by the user. In clinical settings, the monitoring station or remote device may have a display that alerts the clinician to events detected or predicted by the sensor(s), including optical images of the trachea.

Our inventions may be manually calibrated or automatically calibrated. For example, a calibration algorithm may be run when the external sensor assembly is in position on a patient, and it is known that the trachea is free of aspirant.

The algorithm may apply known corrections or offsets to adjust the sensor outputs for the known no-aspirant condition.

Other and further embodiments utilizing one or more aspects of the inventions described herein can be devised by those persons of skill having the benefit of this disclosure without departing from the spirit of our inventions. Further, the various methods and embodiments of the methods of manufacture and assembly of the system, as well as location specifications, can be included in combination with each other to produce variations of the disclosed methods and embodiments. Discussion of singular elements can include plural elements and vice-versa.

The order of steps can occur in a variety of sequences unless otherwise specifically limited. The various steps described herein can be combined with other steps, interlineated with the stated steps, and/or split into multiple steps Similarly, elements have been described functionally and can be embodied as separate components or can be combined into components that have multiple functions.

The inventions have been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by us, but rather, in conformity with the patent laws, we intend to protect fully all such modifications and improvements that come within the scope or range of equivalent of the claims.

The invention claimed is:

1. A system for detecting aspirant, comprising:

a body having an inner surface conforming to at least an anterior portion of a human neck;

a capacitive sensor operably associated with the body and oriented to establish a capacitive trachea detection zone for at least a portion of the trachea lumen when the body is placed about at least the anterior portion of the neck, and comprising an RC circuit operative at a frequency or frequencies between 3 kHz and 3 GHz, inclusive;

an infrared sensor operably associated with the body and oriented to establish an infrared trachea detection zone for at least a portion of the trachea lumen when the body is placed about at least the anterior portion of the neck, and comprising at least one infrared emitter and at least one infrared receiver operative at a wavelength or wavelengths of between 626 nm and 940 nm, inclusive;

a data processor having an input section to receive signals from the capacitive and infrared sensors and operative to determine the presence or absence of aspirant in the capacitive trachea detection zone and/or the infrared trachea detection zone; and a human interface device visually, audibly, and/or physically operative to indicate the presence of aspirant in the trachea.

2. The system of claim 1, wherein the capacitive sensor comprises a plurality of individual capacitive sensors, each sensor operated a frequency or frequencies of between 3 kHz and 3 GHZ, inclusive.

3. The system of claim 2, wherein the plurality of individual capacitive sensors are oriented with respect to the trachea to detect the presence of aspirant, a characteristic of the aspirant, and/or a direction of travel of the aspirant, in the trachea when the body is placed about the anterior portion of the neck.

4. The system of claim 1, wherein the infrared sensor is operated at wavelengths of between 835 nm to 940 nm, inclusive.

5. The system of claim 4, wherein the infrared sensor comprises a plurality of individual infrared sensors, with some individual sensors operated at wavelengths of between 835 nm to 940 nm, inclusive, and other individual infrared sensors operated at wavelengths between 626 nm and 655 nm, inclusive.

6. The system of claim 5, wherein the plurality of individual infrared sensors are operably associated with the body and oriented with respect to the trachea to detect the presence of aspirant, a characteristic of the aspirant, a direction of travel of the aspirant, and/or an image of the aspirant, in the trachea when the body is placed about the anterior portion of the neck.

7. The system of claim 1, wherein the capacitive sensor comprises a plurality of individual capacitive sensors, each individual capacitive sensor operated a frequency of between 3 kHz and 3 GHZ, inclusive, the infrared sensor comprises a plurality of individual infrared sensors, each individual infrared sensor operated at wavelengths of between 835 nm to 940 nm, inclusive, and wherein the capacitive and infrared sensors are operably associated with the body and oriented with respect to the trachea to detect the presence of aspirant, a characteristic of the aspirant, a direction of travel of the aspirant, and/or an image of the aspirant, in the trachea when the body is placed about the anterior portion of the neck.

8. The system of claim 1, comprising an ultrasonic sensor operably associated with the body.

9. The system of claim 8, wherein the capacitive sensor comprises a plurality of individual capacitive sensors, each operated at a frequency of between 3 kHz and 3 GHz, inclusive.

10. The system of claim 9, wherein the plurality of individual capacitive sensors are operably associated with the body and oriented with respect to the trachea to detect the presence of aspirant, a characteristic of the aspirant and/or a direction of travel of the aspirant, in the trachea when the body is placed about the anterior portion of the neck.

11. The system of claim 10, wherein the ultrasonic sensor is operated to emit sound at frequencies of between 1 MHz and 5 MHz, inclusive.

12. The system of claim 11, wherein the ultrasonic sensor is operably associated with the body and oriented with respect to the trachea to detect one or more of: the cricoid cartilage, the presence of aspirant, a characteristic of the aspirant, a direction of travel of the aspirant, and an image of the aspirant.

13. The system of claim 8, wherein the capacitive sensor comprises a plurality of individual capacitive sensors, each individual capacitive sensor is operated a frequency of between 3 kHz and 3 GHz, inclusive, the infrared sensor comprises a plurality of individual infrared sensors, each individual infrared sensor operated at wavelengths of between 625 nm to 940 nm, inclusive, the ultrasonic sensor comprises a plurality of individual ultrasonic sensors, each individual ultrasonic sensor is operated to emit sound at a frequency of between 1 MHz and 5 MHz, inclusive, and wherein all the sensors are operably associated with the body and oriented with respect to the trachea to detect one or more of: the cricoid cartilage, the presence of aspirant, a characteristic of the aspirant, a direction of travel of the aspirant, and/or an image of the aspirant.

14. The system of claim 1, wherein the presence of aspirant in the trachea is indicated to the wearer of the body.

15. The system of claim 1, wherein the data processor is housed within the body.

16. The system of claim 1, wherein the data processor is separate from and remote to the sensor assembly.

17. The system of claim 16, wherein data processor is wired to the sensor assembly for data transmission and power supply.

18. The system of claim 16, wherein the presence of aspirant in the trachea is indicated to a clinician while using the system on a patient.

19. A method of detecting the presence of aspirant, comprising:

providing a body having an inner surface shaped to conform to at least an anterior portion of a human neck;

locating a first sensor in the body so that an operative surface of the first sensor contacts a first portion of the neck when the body is placed on the neck;

locating a second sensor in the body so that an operative surface of the second sensor contacts a second portion of the neck when the body is placed on the neck;

orienting the first and second sensors so that a field of detection of each sensor encompasses at least a portion of a trachea within the neck;

energizing the first and second sensors to generate the first sensor detection field and the second sensor detection field;

processing data from the first and second sensors to detect the presence or absence of aspirant in the trachea without the use of a sensor contrast agent; and automatically indicating the presence of aspirant by one or more of: a visual indication, an audible indication, and a physical indication.

20. The method of claim 19 wherein the first sensor comprises a capacitive sensor and the second sensor comprises an infrared sensor.

21. The method of claim 19 wherein the first sensor comprises a capacitive sensor and the second sensor comprises an infrared sensor, and further comprising an ultrasonic sensor operably associated with the body so that an operative surface of the ultrasonic sensor contacts a third portion of the neck when the body is placed on the neck.

22. The method of claim 21 wherein the capacitive sensor, the infrared sensor and the ultrasonic sensor are oriented such that their respective detection fields traverse substantially the same region of trachea.

23. The method of claim 19, wherein processing data from the first and second sensors is done remotely from the body.

24. The method of claim 19, wherein processing data from the first and second sensors is done within the body.

25. The method of claim 19, wherein automatically indicating comprises vibrating at least a portion of the body.

26. The method of claim 19, wherein automatically indicating comprises visually indicating on a device separate from and remote to the body.

27. The method of claim 26, wherein the device is one or more of: a smart phone, a smart tablet, or a computer.

28. The system of claim 8, wherein the ultrasonic sensor is operated at a frequency or frequencies between 20 kHz and 800 MHz.

29. The system of claim 28, wherein the data processor determines a location of cricoid cartilage.

30. The method of claim 19, further comprising detecting cricoid cartilage and placing the body on the neck based on the detected cricoid cartilage.

* * * * *